United States Patent
Chen et al.

(10) Patent No.: US 7,365,062 B2
(45) Date of Patent: Apr. 29, 2008

(54) NONPEPTIDE SUBSTITUTED SPIROBENZOAZEPINES AS VASOPRESSIN ANTAGONISTS

(75) Inventors: Robert H. K. Chen, Belle Mead, NJ (US); Min A. Xiang, Bridgewater, NJ (US)

(73) Assignee: Ortho McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 11/564,471

(22) Filed: Nov. 29, 2006

(65) Prior Publication Data

US 2007/0117790 A1    May 24, 2007

Related U.S. Application Data

(62) Division of application No. 10/440,914, filed on May 19, 2003, now Pat. No. 7,238,687, which is a division of application No. 09/897,206, filed on Jul. 2, 2001, now Pat. No. 7,001,898.

(60) Provisional application No. 60/216,220, filed on Jul. 5, 2000.

(51) Int. Cl.
*A61K 31/55* (2006.01)
*A61P 9/12* (2006.01)
*C07D 223/16* (2006.01)

(52) U.S. Cl. ............... 514/212.02; 540/586; 540/543

(58) Field of Classification Search ........... 514/212.02; 540/543, 586
See application file for complete search history.

(56) References Cited

U.S. PATENT DOCUMENTS 7,238,687 B2 *   7/2007   Chen et al. ............ 514/212.02

* cited by examiner

*Primary Examiner*—Rebecca Anderson
*Assistant Examiner*—Yong Chu
(74) *Attorney, Agent, or Firm*—Jeremy K. McKown

(57) ABSTRACT

The invention is directed to nonpeptide substituted benzodiazepines of Formula I,

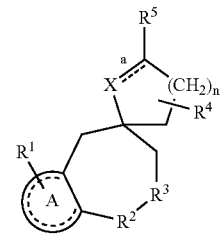

wherein A, X, n, $R^1$, $R^2$, $R^3$, $R^4$, $R^5$, a and b are as described in the specification, which are useful as vasopressin receptor antagonists for treating conditions associated with vasopressin receptor activity such as those involving increased vascular resistance and cardiac insufficiency. Pharmaceutical compositions comprising a compound of Formula I and methods of treating conditions such as hypertension, congestive heart failure, cardiac insufficiency, coronary vasospasm, cardiac ischemia, liver cirrhosis, renal vasospasm, renal failure, cerebral edema and ischemia, stroke, thrombosis, or water retention are also disclosed.

11 Claims, No Drawings

NONPEPTIDE SUBSTITUTED SPIROBENZOAZEPINES AS VASOPRESSIN ANTAGONISTS

CROSS-REFERENCE TO RELATED APPLICATIONS

This is a divisional application of and claims priority to U.S. application Ser. No. 10/440,914, filed May 19, 2003 now U.S. Pat. No. 7,238,687 which is a divisional application of and claims priority to U.S. application Ser. No. 09/897,206 filed Jul. 2, 2001, now issued as U.S. Pat. No. 7,001,898, which claims priority from U.S. provisional application Ser. No. 60/216,220, filed Jul. 5, 2000, the contents of which are hereby incorporated by reference.

FIELD OF THE INVENTION

This invention relates to novel nonpeptide substituted vasopressin receptor antagonists. More particularly, the compounds of the present invention interrupt the binding of the peptide hormone vasopressin to its receptors and are therefore useful for treating conditions involving increased vascular resistance and cardiac insufficiency.

BACKGROUND OF THE INVENTION

Vasopressin is a nonapeptide hormone that is secreted primarily from the posterior pituitary gland. The hormone effects its actions through the vascular V-1 and renal V-2 receptor subtypes. The functions of vasopressin include contraction of uterine, bladder, and smooth muscle; stimulation of glycogen breakdown in the liver; induction of platelet aggregation; release of corticotropin from the anterior pituitary and stimulation of renal water reabsorption. As a neurotransmitter within the central nervous system (CNS), vasopressin can affect aggressive behavior, sexual behavior, the stress response, social behavior and memory. The V-1a receptor mediates central nervous system effects, contraction of smooth muscle and hepatic glycogenolytic effects of vasopressin, while the V-1b receptor mediates anterior pituitary effects of vasopressin. The V-2 receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonpeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at its V-1 receptor in the vasculature, vasopressin V-1 antagonists have reduced blood pressure as a potential treatment for hypertension as well. Thus, vasopressin receptor antagonists are useful as therapeutics in the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

SUMMARY OF THE INVENTION

The present invention is directed to compounds represented by the following Formula I:

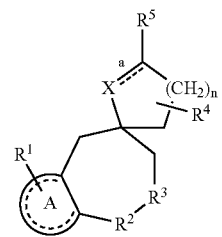

wherein $R^1$ is one to three members independently selected from hydrogen, halogen, amino, substituted amino, hydroxy, alkyloxy, phenyl, substituted phenyl, alkylthio, arylthio, alkyl-sulfoxide, aryl-sulfoxide, alkyl-sulfone, and aryl-sulfone;

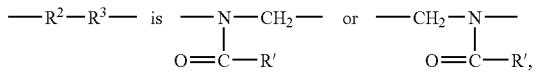

wherein

R' is selected from alkyl, substituted alkyl, phenyl, substituted phenyl, heteroaryl, substituted heteroaryl, and $-B_p-G-E_q-W$ wherein
(a) B is selected from $(CH_2)_m$, NH and O;
(b) G is selected from aryl, substituted aryl, heteroaryl, and substituted heteroaryl;
(c) E is O, S, NH, $(CH_2)_iN(R'')CO$ or $(CH_2)_iCONR''$ wherein R'' is selected from hydrogen, alkyl, and substituted alkyl;
(d) W is one to three members independently selected from hydrogen, alkyl, substituted alkyl, amino, substituted amino, alkylthiophenyl, alkyl-sulfoxidephenyl, aryl, substituted aryl, heteroaryl and substituted heteroaryl;
(e) p is independently 0 or 1;
(f) q is independently 0 or 1;
(g) m is independently 1, 2, or 3; and
(h) i is independently 0, 1, 2, or 3;

$R^4$ is one or two members independently selected from the group consisting of hydrogen, alkyl, substituted alkyl, phenyl, and substituted phenyl;

$R^5$ is selected from hydrogen, alkyl, substituted alkyl, aldehyde, carboxyl, alkoxycarbonyl, substituted alkoxycarbonyl, $-(CH_2)_kNZ^1Z^2$ and $-CONZ^1Z^2$ wherein k is an integer from 1-4, and $Z^1$ and $Z^2$ are independently selected from hydrogen, alkyl, substituted alkyl, heterocyclyl, substituted heterocyclyl, aminocarbonyl, and substituted aminocarbonyl, or N, $Z^1$ and $Z^2$ together form heterocyclyl, substituted heterocyclyl, heteroaryl, or substituted heteroaryl;

a represents a single or double bond provided that when $R^1$ is iodine, bromine, alkylthio, arylthio, alkyl-sulfone, or aryl-sulfone, a is a double bond;

A is selected from aryl, naphthyl and heteroaryl;

X is selected from CH, $CH_2$, CHOH, and C=O; and n is 1, 2, or 3;

or an optical isomer, enantiomer, diastereomer, racemate thereof, or a pharmaceutically acceptable salt thereof.

The compounds of the present invention are vasopressin receptor antagonists which are useful, in general, in disease states of inner ear disorders, hypertension, congestive heart failure, cardiac insufficiency, coronary vasospasm, cardiac ischemia, liver cirrhosis, renal vasospasm, renal failure, cerebral edema and ischemia, stroke, thrombosis, water retention, aggression, obsessive-compulsive disorders, dysmenorrhea, nephrotic syndrome, and central nervous injuries.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An embodiment of the invention is a method of treating a condition associated with vasopressin receptor activity in a subject in need thereof comprising administering to the subject a therapeutically effective amount of any of the compounds or pharmaceutical compositions described above.

Another embodiment of the invention is a method of inhibiting the onset of a condition associated with vasopressin receptor activity in the subject, which comprises administering to the subject a prophylactically effective dose of the pharmaceutical composition of a compound of Formula I.

Further exemplifying the invention is the method of treating congestive heart failure, wherein the therapeutically effective amount of the compound is about 1 to about 30 mg/kg/day.

Still further exemplifying the invention is the method of inhibiting the onset of congestive heart failure, wherein the prophylactically effective amount of the compound is about 1 to about 30 mg/kg/day.

An additional illustration of the invention is a method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof comprising administering to the subject a therapeutically effective amount of any of the compounds or pharmaceutical compositions described above. Preferably, the therapeutically effective amount of the compound administered for treating any of these conditions is about 1 to about 30 mg/kg/day.

Also included in the invention is the use of any of the compounds described above for the preparation of a medicament for treating a condition selected from inner ear disorders, hypertension, congestive heart failure, cardiac insufficiency, coronary vasospasm, cardiac ischemia, liver cirrhosis, renal vasospasm, renal failure, cerebral edema and ischemia, stroke, thrombosis, water retention, aggression, obsessive-compulsive disorders, dysmenorrhea, nephrotic syndrome, and central nervous injuries in a subject in need thereof.

DETAILED DESCRIPTION OF THE INVENTION

The present invention provides nonpeptide substituted spirobenzoazepine compounds which are useful as antagonists of vasopressin. Particularly, these substituted spirobenzoazepine compounds inhibit the binding of vasopressin to V-1a, V-1b, and/or V-2 receptors. The compounds of this invention also show functional activity by their ability to inhibit intracellular calcium mobilization and cAMP accumulation induced by arginine vasopressin (AVP) in transfected HEK-293 cells expressing human V-1a and V-2 receptors. More particularly, the present invention is directed to compounds of Formula I:

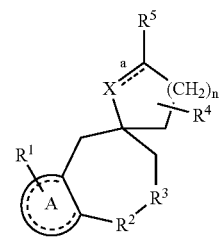

wherein $R^1$ is one to three members independently selected from hydrogen, halogen, amino, substituted amino, hydroxy, alkyloxy, phenyl, substituted phenyl, alkylthio, arylthio, alkyl-sulfoxide, aryl-sulfoxide, alkyl-sulfone, and aryl-sulfone;

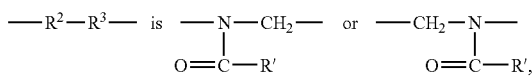

wherein

R' is selected from alkyl, substituted alkyl, phenyl, substituted phenyl, heteroaryl, substituted heteroaryl, and $-B_p-G-E_q-W$ wherein
(a) B is selected from $(CH_2)_m$, NH and O;
(b) G is selected from aryl, substituted aryl, heteroaryl, and substituted heteroaryl;
(c) E is O, S, NH, $(CH_2)_iN(R'')CO$ or $(CH_2)_iCONR''$ wherein R'' is selected from hydrogen, alkyl, and substituted alkyl;
(d) W is one to three members independently selected from hydrogen, alkyl, substituted alkyl, amino, substituted amino, alkylthiophenyl, alkyl-sulfoxidephenyl, aryl, substituted aryl, heteroaryl and substituted heteroaryl;
(e) p is independently 0 or 1;
(f) q is independently 0 or 1;
(g) m is independently 1, 2, or 3; and
(h) i is independently 0, 1, 2, or 3;

$R^4$ is one or two members independently selected from the group consisting of hydrogen, alkyl, substituted alkyl, phenyl, and substituted phenyl;

$R^5$ is selected from hydrogen, alkyl, substituted alkyl, aldehyde, carboxyl, alkoxycarbonyl, substituted alkoxycarbonyl, —$(CH_2)_k NZ^1 Z^2$ and —$CONZ^1 Z^2$ wherein k is an integer from 1-4, and $Z^1$ and $Z^2$ are independently selected from hydrogen, alkyl, substituted alkyl, heterocyclyl, substituted heterocyclyl, aminocarbonyl, and substituted aminocarbonyl, or N, $Z^1$ and $Z^2$ together form heterocyclyl, substituted heterocyclyl, heteroaryl, or substituted heteroaryl;

a represents a single or double bond provided that when $R^1$ is iodine, bromine, alkylthio, arylthio, alkyl-sulfone, or aryl-sulfone, a is a double bond;

A is selected from aryl, naphthyl and heteroaryl;

X is selected from CH, $CH_2$, CHOH, and C=O; and n is 1, 2, or 3;

or an optical isomer, enantiomer, diastereomer, racemate thereof, or a pharmaceutically acceptable salt thereof.

The nonpeptide substituted spirobenzoazepine compounds of the present invention are vasopressin receptor antagonists. In a preferred embodiment, the compounds are orally active. As demonstrated by the results of the pharmacological studies described hereinafter, the compounds show the ability to block vasopressin binding to recombinant V-1a, V-1b, and/or V-2, and therefore are useful as therapeutics in or prophylactics against conditions such as aggression, obsessive-compulsive disorders, hypertension, dysmenorrhea, congestive heart failure/cardiac insufficiency, coronary vasospasm, cardiac ischemia, liver cirrhosis, renal vasospasm, renal failure, edema, ischemia, stroke, thrombosis, water retention, nephrotic syndrome, and central nervous injuries.

In particular, compounds of Formula I, wherein A is phenyl or substituted phenyl are embodiments of the present invention.

More particularly, compounds of Formula I wherein —$R^2$—$R^3$— is

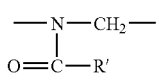

are also particular embodiments of the present invention.

Compounds of Formula I wherein a is a double bond are particular embodiments of the present invention as well.

Compounds of Formula I wherein R' is -$B_p$-G-$E_q$-W wherein B, G, E, W, p, and q are as described hereinabove, are particular embodiments of the present invention. Specific examples are those compounds wherein (a) p is 0 and q is 1;

(b) G is phenyl or substituted phenyl;

(c) E is NHCO; and (d) W is phenyl or substituted phenyl.

Compounds of Formula I wherein $R^5$ is —$CONZ^1 Z^2$, wherein $Z^1$ and $Z^2$ are as described hereinabove, are further particular embodiments of this invention.

Compounds of Formula I wherein R' is phenyl substituted independently with one or more groups selected from alkyl, substituted alkyl, alkoxy, nitro, amino,

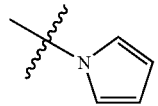

optionally substituted with a group selected from alkyl, substituted alkyl, aldehyde, alkylcarbonyl, carboxyl, alkylcarboxyl, alkoxycarbonyl, and —$NZ^1 Z^2$,

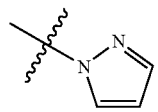

optionally substituted with alkyl or substituted alkyl,

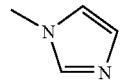

optionally substituted with alkyl or substituted alkyl, —O(CO)O-alkyl, hydroxy, halo, alkyloxycarbonyl, —O-heterocyclyl optionally substituted with optionally substituted alkyl or alkylcarbonyl, and —$NZ^1 Z^2$, wherein $Z^1$ and $Z^2$ are as described hereinabove, are yet particular embodiments of this invention.

Compounds of Formula I wherein X is selected from $CH_2$, CHOH, and C=O are other embodiments of this invention. Particularly, —$R^2$—$R^3$— is

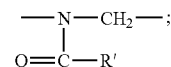

More particularly, $R^1$, $R^4$, and $R^5$ are hydrogen, and R' is substituted phenyl or -$B_p$-G-$E_q$-W wherein (a) W is phenyl or substituted phenyl;

(b) E is NHCO; and (c) p is 0.

Compounds of Formula I wherein n is 1 or 2 are yet other embodiments of this invention. In particular, a is a double bond.

More specifically, the following compounds are particular embodiments of the present invention:

Compound 190: 4-[3-Methoxy-4-(3-hydroxymethylpyrrol-1-yl)benzoyl]-3'-[2-(N,N-dimethylamino)ethylcarboxamido]-4-aza-[6,4]-spiro-[5,6]-benzoundec-2'-ene;

Compounds 22 and 23: (S)-4-(2-fluorophenylbenzoyl-4-aminobenzoyl)-3'-(2-(N,N-dimethylaminoethylaminocarbonyl))-4-aza-[6,4]-spiro-[5,6]-benzoundec-2'-ene and (R)-4-(2-fluorophenylbenzoyl-4-aminobenzoyl)-3'-(2-(N,N-dimethylaminoethylaminocarbonyl))-4-aza-[6,4]-spiro-[5,6]-benzoundec-2'-ene; and Compounds 20 and 21: (S)-4-(2-phenylbenzoyl-4-aminobenzoyl)-3'-(2-(N,N-dimethylaminoethylaminocarbonyl))-4-aza-[6,4]-spiro-[5,6]-benzoundec-2'-ene and (R)-4-(2-phenylbenzoyl-4-aminobenzoyl)-3'-(2-(N,N- dimethylaminoethylaminocarbonyl))-4-aza-[6,4]-spiro-[5,6]-benzoundec-2'-ene.

The compounds of Formula I may be prepared from readily available starting materials in accordance with various known synthetic routes. The present invention is also directed to intermediates of the following formulae,

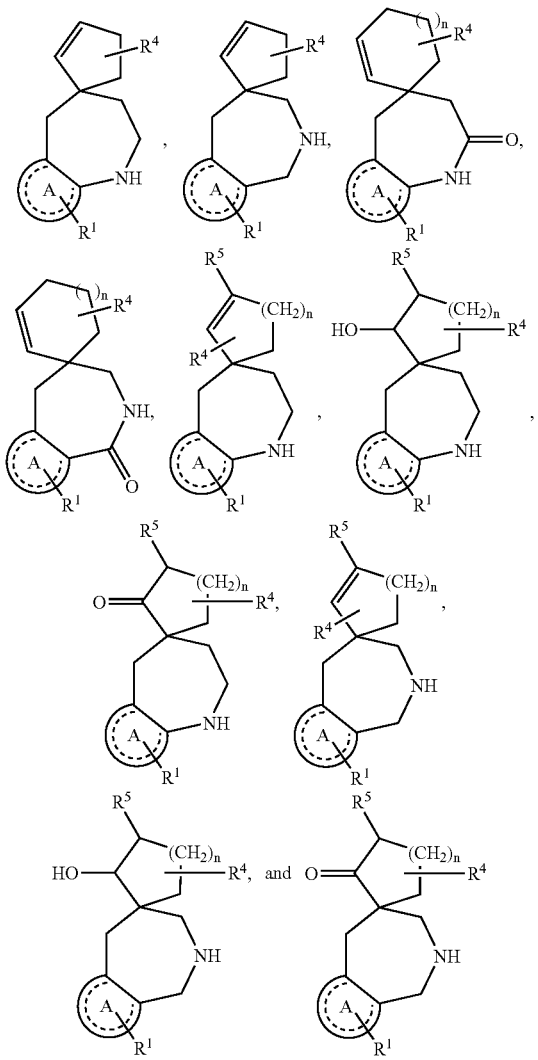

wherein $R^1$, $R^4$, $R^5$, A, and n are as described above.

The compounds of the present invention may also be present in the form of a pharmaceutically acceptable salt or salts. For use in medicine, the salt or salts of the compounds of this invention refer to non-toxic "pharmaceutically acceptable salt or salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc.

Where the compounds according to this invention have at least one stereogenic center, they may accordingly exist as enantiomers. Where the compounds possess two or more stereogenic centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

As used herein, "treating" a disorder means eliminating or otherwise ameliorating the cause and/or effects thereof. To "inhibit" or "inhibiting" the onset of a disorder means preventing, delaying or reducing the likelihood of such onset.

Methods are known in the art for determining therapeutically and prophylactically effective doses for the instant pharmaceutical composition. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. The term "prophylactically effective amount" refers to that amount of active compound or pharmaceutical agent that inhibits in a subject the onset of a disorder as being sought by a researcher, veterinarian, medical doctor or other clinician, the delaying of which disorder is mediated by the reduction of increased vascular resistance.

Unless otherwise noted, under standard nomenclature used throughout this disclosure the terminal portion of the designated side chain is described first, followed by the adjacent functionality toward the point of attachment.

Unless otherwise noted, "alkyl" and "alkoxy" as used herein, whether used alone or as part of a substituent group, include straight and branched chains having 1 to 8 carbon atoms, as well as cycloalkyl groups containing 3 to 8 ring carbons and preferably 5 to 7 ring carbons, or any number within these ranges. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight, branched, or cyclic chain alkyl groups. An alkyl as used herein may be substituted with, for example, amino, substituted amino, halogen, hydroxy, heterocyclyl, substituted heterocyclyl, alkyl, alkoxy, alkoxycarbonyl, heteroaryl, substituted heteroaryl, and/or aryl such as phenyl or benzyl.

"Heterocyclyl" or "heterocycle" is a 3- to 8-member saturated or partially saturated single or fused ring system which consists of carbon atoms and from one to three heteroatoms selected from N, O and S. As used herein, "heterocyclyl" or "heterocycle" also refers to 3-, 4-, 7-, or 8-member unsaturated single or fused ring system which consists of carbon atoms and from one to three heteroatoms selected from N, O and S. The heterocyclyl group may be attached at any heteroatom or carbon atom which results in the creation of a stable structure. Examples of heterocyclyl groups include, but are not limited to pyridine, pyrimidine, oxazoline, pyrrole, imidazole, morpholine, furan, indole, benzofuran, pyrazole, pyrrolidine, piperidine, and benzimidazole. "Heterocyclyl" or "heterocycle" may be substituted with one or more independent groups including, but not limited to, H, halogen, oxo, OH, alkyl, substituted alkyl, amino, heteroaryl, aldehyde, alkylcarbonyl, alkoxycarbonyl, carboxyl, alkylcarboxyl, alkoxy, and $-NZ^1Z^2$ wherein $Z^1$ and $Z^2$ are as described hereinabove.

The term "Ar" or "aryl" as used herein, whether used alone or as part of a substituent group, refers to an aromatic group such as phenyl and naphthyl. When the Ar or aryl group is substituted, it may have one to three substituents which are independently selected from $C_1$-$C_8$ alkyl, $C_1$-$C_8$ alkoxy, aralkoxy, substituted $C_1$-$C_8$ alkyl (e.g., trifluoromethyl), fluorinated $C_1$-$C_8$ alkoxy (e.g., trifluoromethoxy), halogen, cyano, hydroxy, nitro, optionally substituted amino, carboxyl, alkylcarboxyl, alkoxycarbonyl, $C_1$-$C_4$ alkylamino (i.e., $-NH-C_1$-$C_4$ alkyl), $C_1$-$C_4$ dialkylamino (i.e., $-N-[C_1$-$C_4$ alkyl]$_2$ wherein the alkyl groups can be the same or different), $-O(CO)O$-alkyl, $-O$-heterocyclyl optionally substituted with optionally substituted alkyl or alkylcarbonyl (i.e.,

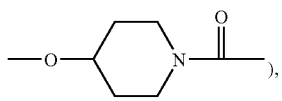), optionally substituted heteroaryl (i.e.,

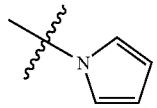

optionally substituted with a group selected from alkyl, substituted alkyl, aldehyde, alkylcarbonyl, carboxyl, alkylcarboxyl, alkoxycarbonyl, and $-NZ^1Z^2$ wherein $Z^1$ and $Z^2$ are as described hereinabove), and unsubstituted, mono-, di- or tri-substituted phenyl wherein the substituents on the phenyl are independently selected from aryl, $C_1$-$C_8$ alkyl, $C_1$-$C_8$ alkoxy, substituted $C_1$-$C_8$ alkyl, fluorinated $C_1$-$C_8$ alkoxy, halogen, cyano, hydroxy, amino, nitro, carboxyl, alkylcarboxyl, alkylamino, dialkylamino and heteroaryl. "Ph" or "PH" denotes phenyl.

The term "heteroaryl" as used herein represents a stable five or six-membered monocyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Prefered heteroaryl groups include pyridinyl, thiophenyl, furanyl and quinolinyl. When the heteroaryl group is substituted, the heteroaryl group may have one to three substituents which are independently selected from $C_1$-$C_8$ alkyl, substituted $C_1$-$C_8$ alkyl, halogen, aldehyde, alkylcarbonyl, aryl, heteroaryl, alkoxy, alkylamino, dialkylamino, arylamino, nitro, carboxyl, alkylcarboxyl, and hydroxy.

The term "aralkoxy" indicates an alkoxy group substituted with an aryl group (e.g., benzyloxy).

The term "acyl" as used herein, whether used alone or as part of a substituent group, means an organic radical having 2 to 6 carbon atoms (branched or straight chain) derived from an organic acid by removal of the hydroxyl group.

The term "Ac" as used herein, whether used alone or as part of a substituent group, means acetyl.

The term "halogen" shall include iodine, bromine, chlorine and fluorine.

The terms "substituted alkylcarboxy," "substituted amino," and "substituted aminocarbonyl" denote substitution of said groups with at least one member selected from halogen, alkyl, substituted alkyl, aryl, alkoxy, amino, and substituted amino.

Whenever the term "alkyl", "acyl", or "aryl" or either of their prefix roots appear in a name of a substituent (e.g., aralkyl, dialkylamino), it shall be interpreted as including those limitations given above for "alkyl", "acyl", and "aryl." Designated numbers of carbon atoms (e.g., $C_1$-$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The utility of the compounds to treat disorders of increased vascular resistance can be determined according to the procedures described herein. The present invention therefore provides a method of treating vascular resistance disorders in a subject in need thereof which comprises administering any of the compounds as defined herein in a quantity effective to treat vascular resistance disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of Formula I or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 1 mg to 30 mg/kg and may be given at a dosage of from about 1 to 30 mg/kg/day (preferred 3 to 15 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a stereogenic HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, Third Edition, John Wiley & Sons, 1999. The protecting groups may be removed at a convenient subsequent stage using methods known from the art.

This invention will be better understood by reference to the schemes and examples that follow, but those skilled in the art will readily appreciate that these are only illustrative of the invention as described more fully in the claims which follow thereafter.

Scheme 1

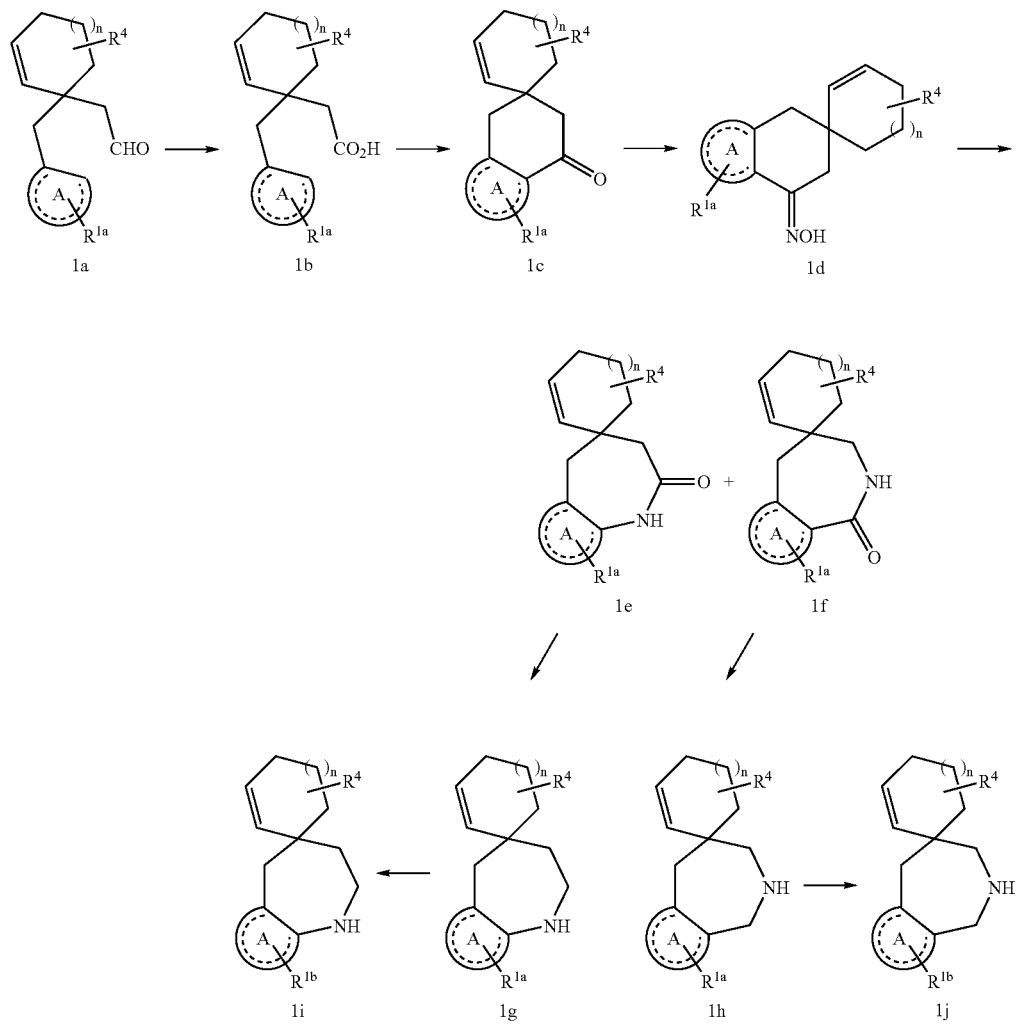

As set forth in Scheme 1, wherein $R^{1a}$ is $R^1$ other than $R^{1b}$, $R^{1b}$ is alkyl-sulfoxide, aryl-sulfoxide, alkyl-sulfone, or aryl-sulfone, and $R^1$, $R^4$, A, and n are as described above, an aldehyde 1a (may be easily prepared by using as starting materials, which is either commercially available or may be easily prepared by known methods, and following scheme 1 in U.S. Pat. No. 5,753,715 to Chen et al.) is oxidized with an oxidation reagent such as $CrO_3$—$H_2SO_4$ in acetone or pyridinium chlorochromate in dimethylformamide (DMF) or $NaClO_2$ in dimethylsulfoxide (DMSO) and water at a temperature preferably between 0° C. and room temperature (rt) to give the corresponding acids 1b. Cyclization of the acids with an acid anhydride such as $(CF_3CO)_2$O—$CF_3CO_2H$ at a temperature preferably between 0° C. and room temperature produces the ketones 1c. Beckmann rearrangement of the ketone via oxime 1d followed by $SOCl_2$ in dioxane preferably at room temperature gives lactams 1e and 1f. Alternatively, the reaction may be carried out with $NaN_3$ in $CF_3CO_2H$ to give primarily lactam 1e. Lactams 1e and 1f can be easily separated by column chromatography on silica gel. Lactam 1e can also be separated into enantiomer by chiral HPLC column or other methods known in the art. Reduction of lactams 1e or 1f with an agent such as lithium aluminum hydride (LAH) in ether at a temperature preferably between 0° C. and room temperature produces amines 1g and 1h, respectively. Amines 1g and 1h wherein $R^{1a}$ is alkylthio or arylthio may be further converted to amines 1i and 1j wherein $R^{1b}$ is alkyl-sulfoxide or aryl-sulfoxide, respectively, with an oxidizing agent such as sodium periodate in a solvent such as methanol or ethanol preferably between room temperature and 60° C. Amines 1g and 1h wherein $R^{1a}$ is alkylthio or arylthio may also be converted to amines 1i and 1j wherein $R^{1b}$ is alkyl-sulfone or aryl-sulfone, respectively, with an oxidizing agent such as $H_2O_2$.

Scheme 2

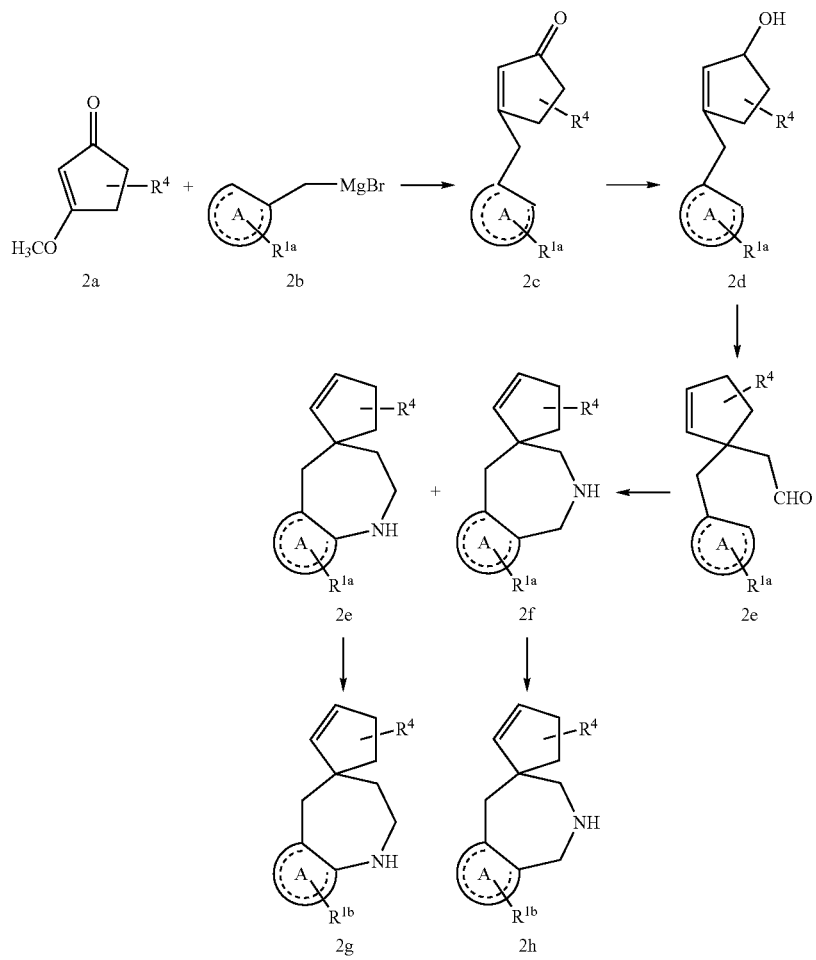

As set forth in Scheme 2, wherein $R^{1a}$, $R^{1b}$, $R^4$, and A are as described above, amines 2e through 2h may be made from 2a and 2b, which are either commercially available or may be easily prepared by known methods, in a manner similar to scheme 1.

Scheme 3

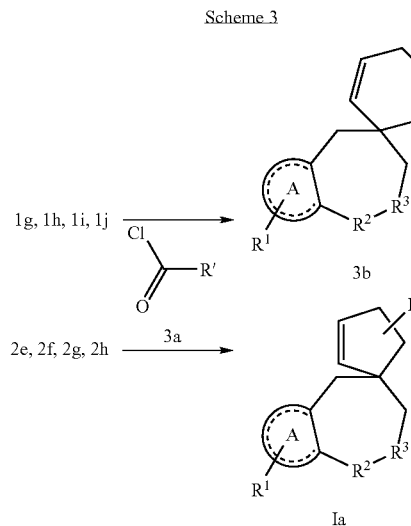

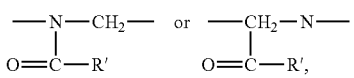

As set forth in Scheme 3, wherein $R^1$, $R^2$, $R^3$, R', A, and n are as described above, treatment of amines 1g, 1h, 1i, or 1j with an acid halide or acid anhydride such as acid chlorides (3a) in an organic solvent such as tetrahydrofuran (THF), $CH_2Cl_2$, or $CHCl_3$ with an organic base such as $Et_3N$ or inorganic base such as $K_2CO_3$ at a temperature preferably between 0° C. and room temperature produces amides 3b. The same treatment of amines 2e, 2f, 2g, or 2h produces amides Ia.

Alternatively, compounds Ia and 3b wherein —$R^2$—$R^3$— is $$-\underset{\underset{\underset{R'}{C}}{\overset{\|}{O=}}}{N}-CH_2- \quad \text{or} \quad -CH_2-\underset{\underset{\underset{R'}{C}}{\overset{\|}{O=}}}{N}-,$$

and R' is 4-nitro phenyl (may have, in addition, one or more appropriate substituents) can be prepared from amines 1g, 1h, 1i, 1j, 2e, 2f, 2g, or 2h and 4-nitro benzoyl acid chloride, followed by a reduction such as hydrogenation with 10% Pd/C or a reduction with a reducing agent such as $SnCl_2$. The amines obtained can be treated with an appropriate acid chloride or isocyanates to give the corresponding compounds of Formula I.

Scheme 4

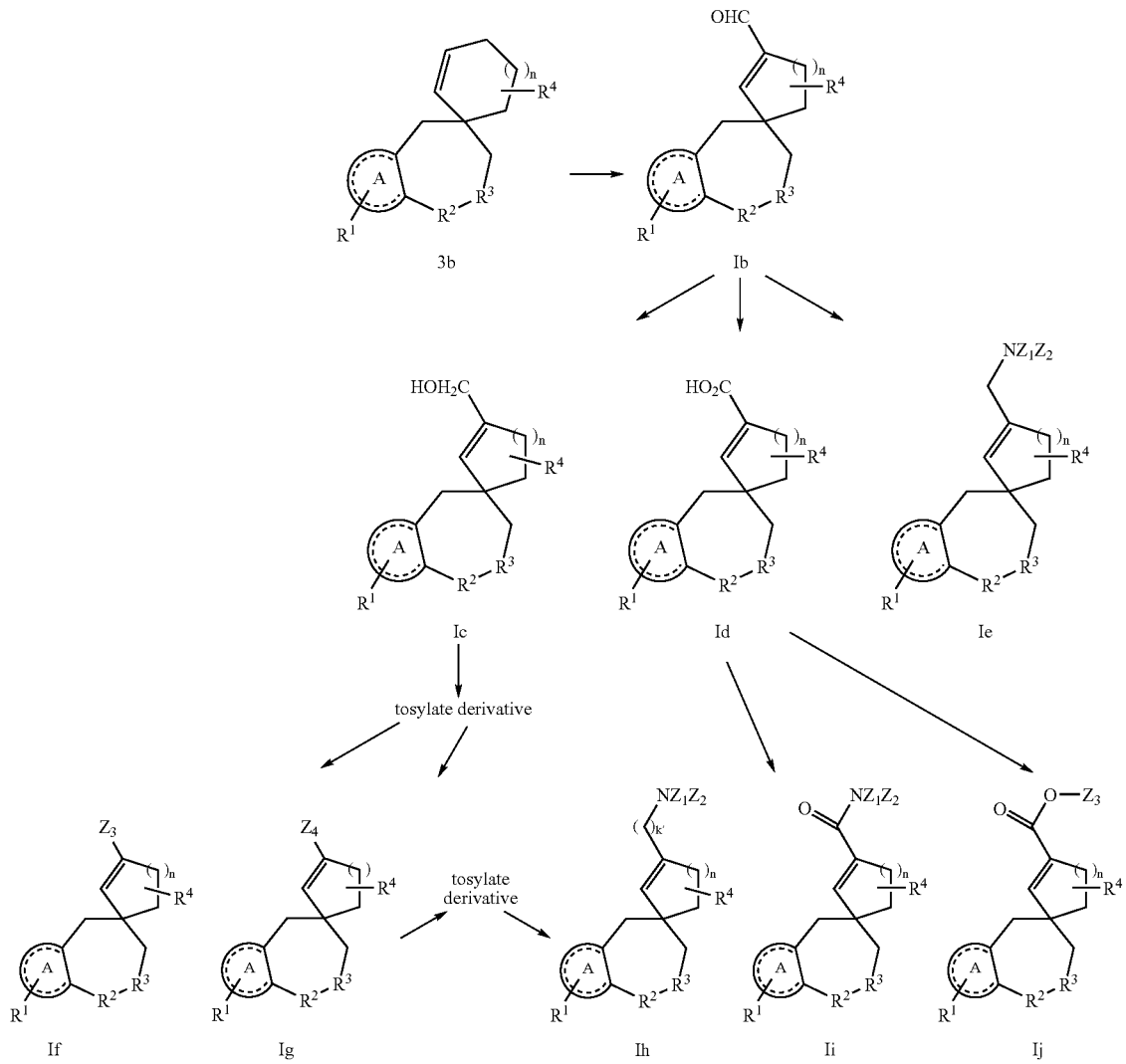

As set forth in Scheme 4, wherein $Z_3$ is alkyl or substituted alkyl, $Z_4$ is hydroxy $C_{2-8}$ alkyl, k' is 2-4, and $R^1$, $R^2$, $R^3$, $Z_1$, $Z_2$, A, and n are as described above, compounds 3b are treated with an excess of ozone at a temperature preferably between −78 and −20° C. in an organic solvent such as methanol (MeOH), $CH_2Cl_2$, ethyl acetate (EtOAc) or $CHCl_3$. The ozonides formed in the same container can be treated with a reducing reagent such as methyl sulfide or triphenyl phosphine to give bis aldehydes. These intermediates, without further purification, are cyclized with an organic acid such as toluenesulfonic acid or methylsulfonic acid at a temperature preferably between 0° C. and room temperature to give the corresponding aldehydes Ib. Reduction of aldehydes Ib with a reducing agent such as $NaBH_4$ (in $CH_3OH$ or EtOH) or $NaBH(OAc)_3$ at a temperature preferably between 0° C. and room temperature gives the corresponding alcohols Ic. Oxidation of Ib with an oxidation reagent such as $CrO_3$—$H_2SO_4$ or $NaClO_2$-DMSO at a temperature preferably between −20° C. and room temperature produces the corresponding acids Id. Reductive amination of Ib with an amine with a reagent such as $NaCNBH_3$ in $CH_3OH$ and acetic acid at a temperature preferably between 0° C. and room temperature gives amines Ie. Treatment of the alcohol Ic with an appropriate sulfonyl chloride such as tosyl chloride and triethylamine in an organic solvent such as $CH_2Cl_2$ gives a tosylate derivative. Reacting the tosylate derivative with an appropriate reagent such as dialkyl or diaryl copper lithium or copper hydride in THF will give the corresponding compounds of If. Alternatively, reacting the tosylate derivative with an appropriate cyanide such as NaCN or KCN followed by hydrolysis will give the corresponding acid, which can be further reduced with an agent such as $BH_3$-THF complex at a low temperature preferably from −78 to 0° C. to produce the corresponding alcohol Ig (Repeating the same steps will further extend the alkyl chain). Alcohol Ig may be further converted to compounds of Ih. Treatment of the alcohol Ig with an appropriate sulfonyl chloride such as tosyl chloride and triethylamine in an organic solvent such as $CH_2Cl_2$ gives a tosylate derivative. Reacting the tosylate derivative with an appropriate reagent such as $HNZ^1Z^2$ (known compounds) will give the corresponding compounds of Ih. Coupling of acids Id with various amines produces the corresponding amide derivatives Ii. Acids Id may also be converted to compounds of Ij in the presence of an acid such as $H_2SO_4$ with $Z_3OH$, which is either commercially available or may be easily prepared by known methods.

Alternatively, compounds Ib through Ij wherein —$R^2$—$R^3$— is

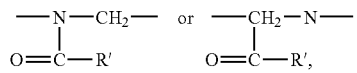

and R' is 4-nitro phenyl 4-nitro phenyl can be prepared from amines 1g, 1h, 1i, 1j, 2e, 2f, 2g, or 2h and 4-nitro benzoyl acid chloride via ozonization and cyclization as described above followed by reduction such as hydrogenation with 10% Pd/C or reduction with a reducing reagent such as $SnCl_2$. The amines obtained can be treated with an appropriate acid chloride or isocyanates to give the corresponding compounds of Formula I.

Scheme 5

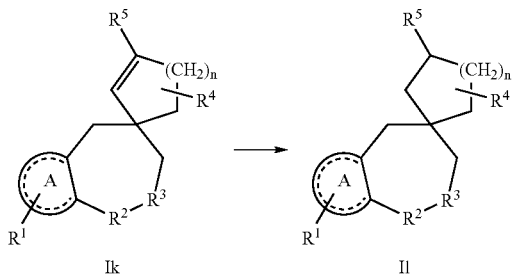

As set forth in Scheme 5, wherein $R^1$, $R^2$, $R^3$, $R^4$, $R^5$, A, and n are as described above, prolonged hydrogenation of amides Ik with $H_2$ at preferably 30-50 psi in an organic solvent such as methanol, ethanol or ethyl acetate at room temperature in the presence of catalyst such as Pd/C gives Il.

Scheme 6

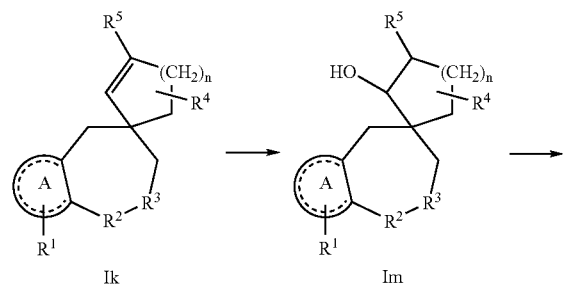

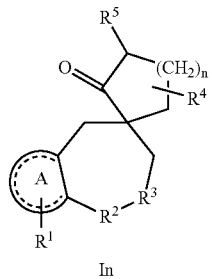

As set forth in Scheme 6, wherein $R^1$, $R^2$, $R^3$, $R^4$, $R^5$, A, and n are as described above, hydroboration of amides Ik with an agent such as $BH_3$-THF in an organic solvent such as THF at a temperature preferably between $-78°$ C. and room temperature followed by $H_2O_2$—NaOH can produce the corresponding alcohols Im. Oxidation of these alcohols with $CrO_3$—$H_2SO_4$ or $CrO_3$-pyridine at a temperature preferably between $-20°$ C. and room temperature will give ketones In.

The method of treating vascular resistance disorders described in the present invention may also be carried out using a pharmaceutical composition comprising any of the compounds as defined herein and a pharmaceutically acceptable carrier. The pharmaceutical composition may contain between about 100 mg and 1000 mg, preferably about 100 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms can be in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolyl-ysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of vascular resistance is required.

The daily dosage of the products may be varied over a wide range from 100 to 3000 mg per adult human per day. For oral administration, the compositions are preferably provided in the form of tablets containing the active ingredient in the amount sufficient for the symptomatic adjustment of the dosage to the patient to be treated. An effective amount of the drug is ordinarily supplied at a dosage level of from about 1 mg/kg to about 30 mg/kg of body weight per day. Preferably, the range is from about 3 to about 15 mg/kg of body weight per day, most preferably, from about 5 to about 10 mg/kg of body weight per day. The compounds may be administered on a regimen of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following examples are intended to illustrate the invention but not to limit it.

EXAMPLE 1

3-Benzyl-3-carboxymethylcyclohexene

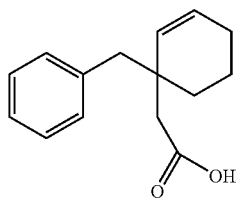

To a mixture of $NaH_2PO_4$ (55.3 g), $NaClO_2$ (36.3 g), DMSO (200 mL) and water (375 mL) was added a solution of 3-benzyl-3-formylmethylcyclohexene (57 g) in DMSO (150 mL) during a 3 hour period. After addition, the mixture was stirred overnight and diluted with ether (200 mL). This was extracted with saturated $NaHCO_3$ (3×100 mL). The combined aqueous layer was cooled to 0° C. and acidified to PH=1 with conc. HCl. This was extracted with $CH_2Cl_2$ (3×300 mL). The combined organic layer was dried ($Na_2SO_4$) and the solvent was removed in vacuo. The residue was purified by column chromatography on silica gel to give the title compound as thick oil (50 g). MS ($MH^+$=231).

EXAMPLE 2

3-Oxo-[5,5]-spiro-[4,5]-benzoundec-2'-ene

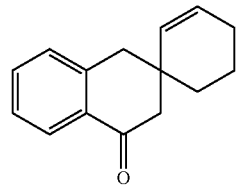

To a solution of $CF_3CO_2H$ (47.5 g) and $(CF_3CO)_2O$ (42.3 g) in $CH_2Cl_2$(100 mL) was added a solution of 3-benzyl-3-carboxymethylcyclhexene (46.35 g) in $CH_2Cl_2$ (5 mL) at 0° C. under $N_2$ and stirred for 10 minutes. The resulting mixture was allowed to warm to room temperature and stirred for two more hours. This was carefully treated with saturated $K_2CO_3$ (40 mL) and the organic layer was separated and the aqueous layer was extracted with ether (3×300 mL). The combined organic layer was dried ($Na_2SO_4$) and the solvent was removed in vacuo. The residue was filtered through a short silica gel column and washed with (EtOAc: hexane 1:9) to give the title compound as a thick yellow oil (42.7 g). MS ($MH^+$=213).

EXAMPLE 3

3-Hydroxyimino-[5,5]-spiro-[4,5]-benzoundec-2'-ene

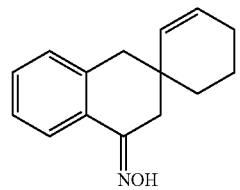

A mixture of 3-oxo-[5,5]-spiro-[4,5]-benzoundec-2'-ene (2.3 g), $NH_2OH$:HCl (1.24 g) and pyridine (1.42 g) in ethanol (25 mL) was heated at 45° C. (bath temperature) and stirred for 4 hours. Most of solvent was removed in vacuo and the residue was diluted with $CH_2Cl_2$ (300 mL). This was washed with cold 1 N. HCl(2×50 mL) and $H_2O$ (50 mL) and then dried ($Na_2SO_4$). The solvent was removed in vacuo to give a solid and this was crystallized from $CH_2Cl_2$/hexane to give the oxime as white powder. MS ($MH^+$=228).

EXAMPLE 4

Procedure to prepare 4-aza-3-oxo-[6,5]-spiro-[5,6]-benzododec-2'-ene and 3-aza-4-oxo-[6,5]-spiro-[5,6]-benzododec-2'-ene

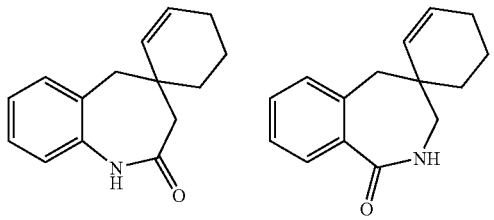

To a solution of 3-hydroxyimino-[5,5]-spiro-[4,5]-benzoundec-2'-ene (2.1 g) in dioxane was added SOCl₂ (2.8 g) slowly at room temperature (rt) under N₂ and stirred for 16 hours.

The resulting mixture was poured into ice water (100 mL) and stirred for 30 minutes. The organic was separated and the aqueous layer was extracted with ether (3×75 mL). The combined organic layer was dried (Na₂SO₄) and the solvent was removed in vacuo. The residue was purified by column chromatography on silica gel (350 g). Elution with EtOAc:hexane 1:1 gave 4-aza-3-oxo-[6,5]-spiro-[5,6]-benzododec-2'-ene (220 mg) as off-white powder. MS (MH⁺=228). Elution with EtOAc gave 3-aza-4-oxo-[6,5]-spiro-[5,6]-benzododec-2'-ene(1.2 g) as white powder. MS (MH⁺=228).

Alternative procedure to prepare 4-aza-3-oxo-[6,5]-spiro-[5,6]-benzododec-2'-ene To a mixture of 3-oxo-[5,5]-spiro-[4,5]-benzoundec-2'-ene (31 g) and CF₃CO₂H (130 mL) was added NaN₃ (19 g) at 55° C. in several portions and stirred for 16 hours. The resulting mixture was allowed to cool to room temperature and most of solvent was removed in vacuo. The residue was diluted with EtOAc (300 mL) and was poured carefully into saturated NaHCO₃ (300 mL). The organic layer was separated and aqueous layer was extracted with EtOAc (300 mL). The combined organic layer was dried (Na₂SO₄) and the solvent was removed in vacuo. The residue was purified by column chromatography on silica gel (850 g, EtOAc:hexane 3:7) to give 4-aza-3-oxo-[6,5]-spiro-[5,6]-benzododec-2'-ene (23.5 g) as off-white powder. MS (MH⁺=228).

EXAMPLE 5

4-Aza-[6,5]-spiro-[5,6]-benzododec-2'-ene

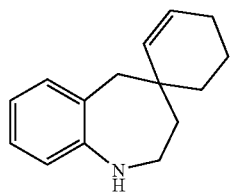

To a suspension of LAH (2.03 g) in ether (400 mL) was added 4-aza-3-oxo-[6,5]-spiro-[5,6]-benzododec-2'-ene (9.9 g) in three portions at room temperature under N₂ and stirred overnight. The mixture was cooled to 0° C. and the saturated K₂CO₃ was carefully added until white precipitate formed. The resulting mixture was filtered through a pad of Celite and washed with CH₂Cl₂ (2×200 mL). The combined filtrate was concentrated in vacuo to give a thick yellow oil (9.41 g). MS (MH⁺=214).

EXAMPLE 6

4-(4-Nitrobenzoyl)-4-aza-[6,5]-spiro-[5,6]-benzododec-2'-ene (Compound 49)

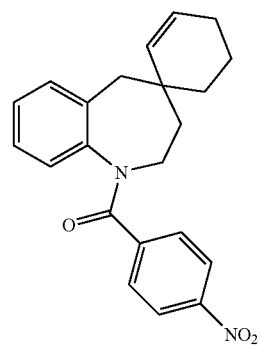

To a solution of 4-aza-[6,5]-spiro-[5,6]-benzododec-2'-ene (8.5 g), Et₃N in CH₂Cl₂ (350 mL) was added a solution of 4-nitrobenzoyl chloride (7.2 g) in CH₂Cl₂ (50 mL) dropwise at room temperature under N₂ and the resulting mixture was stirred for 16 hr. This was poured into cold 1N NaOH (100 mL) and the organic layer was separated and the aqueous layer was extracted with CH₂Cl₂ (2×100 mL). The combined organic layer was dried (Na₂SO₄). The solvent was removed in vacuo to give the title compound as a pale yellow solid (12.5 g). NMR(CDCl₃): 1.98 (m, 2H), 2.72 (Abq, J=12 Hz, 2H), 3.23 (m, 2H), 5.65 (m, 2H, olefinic protons), 6.70~7.15 (m, 4H, aromatic protons), 7.30 (d, J=6 Hz, 2H), 8.15 (d, J=6 Hz, 2H).

EXAMPLE 7

4-(4-Nitrobenzoyl)-3'-(formyl)-4-aza-[6,4]-spiro-[5,6]-benzoundec-2'-ene

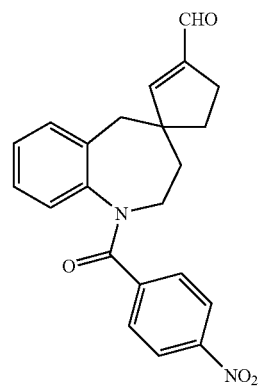

To a solution of 4-(4-nitrobenzoyl)-4-aza-[6,5]-spiro-[5,6]-benzododec-2'-ene in methylene chloride was treated with ozone at −78° C. The excess of ozone was removed with a stream of nitrogen and the resulting mixture was treated with methyl sulfide followed by TsOH—H₂O. The mixture was allowed to warm to room temperature and stirred for 48 hr. The mixture was poured into cold 1 N NaOH (100 mL) and the organic layer was separated and the aqueous layer was extracted with methylene chloride (2×100 mL). The combined organic was dried (Na$_2$SO$_4$) and the solvent was removed in vacuo. The oily residue was purified by column chromatography on silica gel (300 g, EtOAc/Hexane 1:1) to give the title compound as colorless crystals (mp 90–93° C. NMR(CDCl$_3$): 3.45 (s, 2H, benzylic protons), 5.83 (bs, 1H, olefinic proton), 7.22 (m, 5H, aromatic protons).

EXAMPLE 8

4-(4-Nitrobenzoyl)-3'-(carbomethoxy)-4-aza-[6,4]-spiro-[5,6]-benzoundec-2'-ene

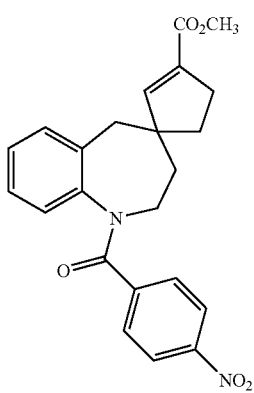

To a solution of CrO$_3$, conc. H$_2$SO$_4$ in H$_2$O and acetone was added a solution of aldehyde in acetone at 0° C. during 1 hour period. After addition, the mixture was treated with water and the organic layer was separated. The aqueous layer was extracted with CH$_2$Cl$_2$ (2×200 mL). The combined organic layer was dried (Na$_2$SO$_4$) and the solvent was removed in vacuo. The residue was re-dissolved in methanol and treated with an excess of trimethylsilyldiazomethane. The solvent was removed in vacuo and the residue was purified by column chromatography on silica gel (100 g, EtOAc/hexane (4:6).to give 3 as colorless crystals, mp. 172-174° C.; NMR(CDCl3): 3.72 and 3.77 (both s, 3H total, CH$_3$O—), 6.42 and 6.71 (both s, 1H total, olefinic proton).

EXAMPLE 9

4-(4-Aminobenzoyl)-3'-(carbomethoxy)-4-aza-[6,4]-spiro-[5,6]-benzoundec-2'-ene

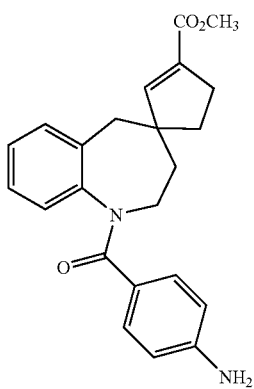

A mixture of 4-(4-nitrobenzoyl)-3'-(carbomethoxy)-4-aza-[6,4]-spiro-[5,6]-benzoundec-2'-ene, conc HCl, 10% Pd/C was hydrogenated at 50 psi for 3 hours. The resulting mixture was filtered through a pad of Celite and washed with CH$_2$Cl$_2$ (250 mL). The combined filtrate was concentrated in vacuo to give the title compound as white powder (270 mg, 24%), mp 96-98° C. as a light brown powder. MS (m+1)= 379.

Alternative Procedure

A mixture of 4-(4-nitrobenzoyl )-3'-(carbomethoxy)-4-aza-[6,4]-spiro-[5,6]-benzoundec-2'-ene and SnCl$_2$ in ethanol was heated to reflux under nitrogen for 12 hours. The mixture was allowed to cool to room temperature and saturated NaHCO$_3$ was added. This was filtered through a pad of Celite and washed several portions with CH$_2$Cl$_2$. The combined filtrate was conc. in vacuo to give the title compound. MS (m+1)=359.

EXAMPLE 10

4-(2-Phenylbenzoyl-4-aminobenzoyl)-3'(carbomethoxy)-4-aza-[6,4]-spiro-[5,6]-benzoundec-2'-ene

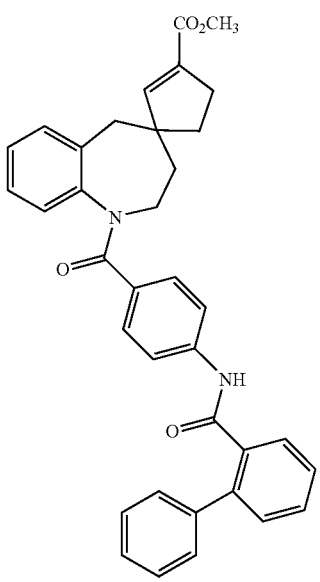

To a solution of aniline (Example 9), Et$_3$N in CH$_2$Cl$_2$ was added a solution of 2-phenylbenzoyl chloride in CH$_2$Cl$_2$ at 0° C. under nitrogen during 15 min. period. After addition, the mixture was allowed to warm to room temperature and stirred for another hour. The mixture was poured into cold 1 N. NaOH (100 mL). The organic layer was separated and the aqueous was extracted with CH$_2$Cl$_2$ (2×100 mL). The combined organic layer was dried (Na$_2$SO$_4$) and the solvent was removed in vacuo. The oily residue was purified by column chromatography on silica gel. NMR(CDCl₃): 3.20 (Abq, J=8 Hz, 2H), 5.63 (s, 1H, olefinic proton), 6.61 (bs, 1H, NH)., mp 90-92° C. MS (MH⁺=540)

EXAMPLE 11

4-(2-Phenylbenzoyl-4-aminobenzoyl)-3'(carboxyl)-4-aza-[6,4]-spiro-[5,6]-benzoundec-2'-ene (Compound 4)

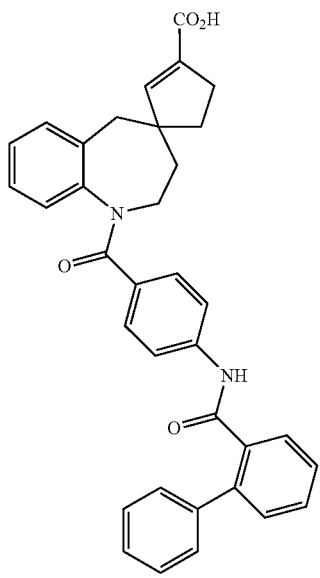

A mixture of the ester (Example 10), methanol (150 mL) and 1 N NaOH (50 mL) was stirred at room temperature under nitrogen for 16 hr. Most of methanol was removed in vacuo and the residue was dilute with water and ether. The aqueous layer was separated and the organic layer was extracted with 0.5 NaOH (50 mL). The combined aqueous layer was cooled to 0° C. and acidified to PH=1 with conc. HCl. This was extracted with CH₂Cl₂ (3×100 mL). The combined organic layer was dried (Na₂SO₄) and solvent was removed in vacuo to give the title compound as an off-white powder. MS (MH⁺=543).

EXAMPLE 12

4-(2-Phenylbenzoyl-4-aminobenzoyl)-3'-[2-(N,N-dimethylaminoethylcarbonyl)]-4-aza-[6,4]-spiro-[5,6]-benzoundec-2'-ene (Compound 9)

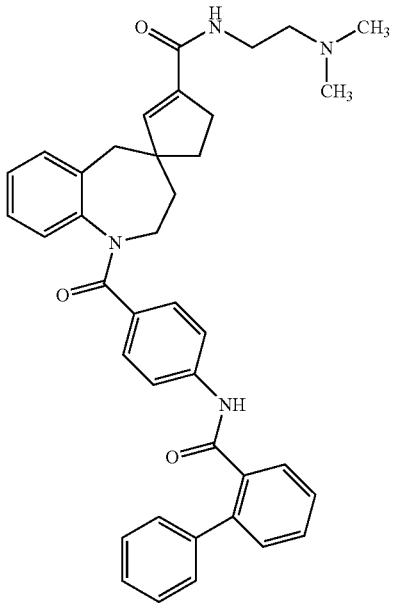

A mixture of the acid (Example 11) and SOCl₂ in CH₂Cl₂ was stirred at room temperature for 16 hour. The excess SOCl₂ and solvent were removed in vacuo and residue was dissolved in toluene and the solvent was removed in vacuo. The residue was again re-dissolved in CH₂Cl₂ and was added to a solution of N, N-dimethylaminoethylamine and triethyl amine in CH₂Cl₂ and room temperature under nitrogen and stirred for four hours. The resulting mixture was treated with CH₂Cl₂ and 1N NaOH (100 mL). The organic layer was separated and the aqueous layer was extracted with CH₂Cl₂ (2×50 mL). The combined organic layer was dried (Na₂SO₄) and the solvent was removed in vacuo. The oily residue was purified by column chromatography on silica gel (400 g, ethyl acetate:methanol:triethyl amine 100:10:1) to give the title compound as off-white powder. MS (MH⁺=613)

EXAMPLE 13

4-(2-Phenylbenzoyl-4-aminobenzoyl)-4-aza-[6,5]-spiro-[5,6]-benzododec-2'-ene (Compound 66)

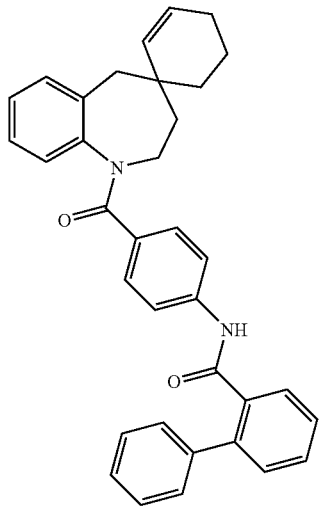

The procedure of Example 6 was followed, but 4-nitrobenzoyl chloride was substituted with 4-(2-phenylbenzoylamido)benzoyl chloride the title compound was obtained as colorless solid. MS (MH$^+$=513).

EXAMPLE 14

4-(2-Phenylbenzoyl-4-aminobenzoyl)-3'-(formyl)-4-aza-[6,4]-spiro-[5,6]-benzoundec-2'-ene

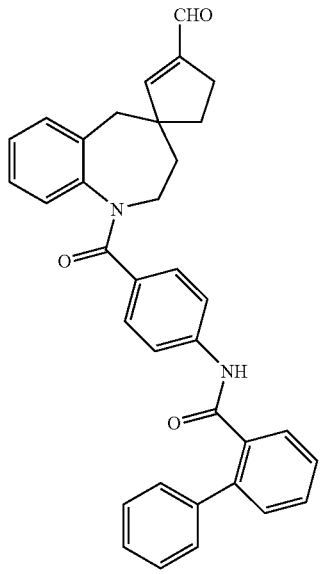

The procedure of Example 7 was followed, but 4-(4-nitrobenzoyl)-4-aza-[6,5]-spiro-[5,6]-benzododec-2'-ene was substituted with 4-(4-phenylbenzoyl)-4-aza-[6,5]-spiro-[5,6]-benzododec-2'-ene. The title compound was obtained as colorless solid. MS (MH$^+$=527).

EXAMPLE 15

4-(2-Phenylbenzoyl-4-aminobenzoyl)-3'-(hydroxymethyl)-4-aza-[6,4]-spiro-[5,6]-benzoundec-2'-ene (Compound 1)

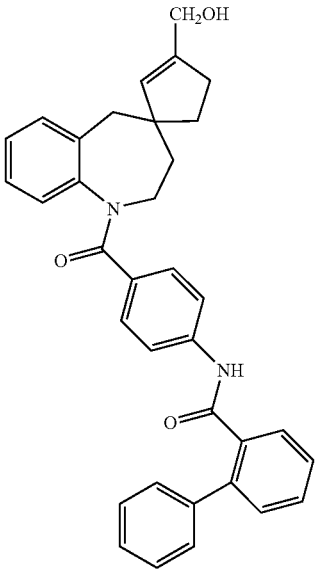

To a solution of 4-(2-phenylbenzoyl-4-aminobenzoyl)-3-(formyl)-4-aza-[6,4]-spiro-[5,6]-benzoundec-2'-ene (Example 14) in CH$_3$OH was added NaBH$_4$ all at once at room temperature under nitrogen and stirred for 1 hour. The resulting mixture was treated with 1 N NaOH (50 mL) and stirred for 30 minutes. Most of CH$_3$OH was removed in vacuo and residue was diluted with H$_2$O and CH$_2$Cl$_2$. The organic layer was separated and the aqueous layer was extracted with CH$_2$Cl$_2$ (2×100 mL). The combined organic layer was dried (Na$_2$SO$_4$) and the solvent was removed in vacuo to give the title compound as white powder. MS (MH$^+$=529).

EXAMPLE 16

4-(2-Phenylbenzoyl-4-aminobenzoyl)-3'-(methylaminomethyl)-4-aza-[6,4]-spiro-[5,6]-benzoundec-2'-ene (Compound 3)

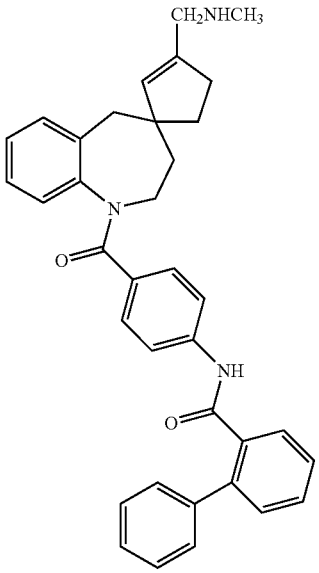

To a solution of 4-(2-phenylbenzoyl-4-aminobenzoyl)-3'-(formyl)-4-aza-[6,4]-spiro-[5,6]-benzoundec-2'-ene (31 mg, Example 14), CH$_3$NH$_2$ (40% aqueous solution, 0.3 mL) and acetic acid (0.5 mL) in CH$_3$OH (5 mL) was added NaCNBH$_3$ (21 mg) all at once at room temperature under nitrogen and stirred for 2 hours. The volatile material was removed in vacuo and the residue was treated with 1 N NaOH (30 mL) and CH$_2$Cl$_2$ (50 mL). The organic layer was separated and the aqueous layer was extracted with CH$_2$Cl$_2$ (2×10 mL). The combined organic layer was dried (Na$_2$SO$_4$) and concentrated in vacuo to give the title compound as pale yellow oil (30 mg). MS (MH$^+$=542). This was converted into hydrochloride salt as a white powder.

EXAMPLE 17

4-(2-Phenylbenzoyl-4-aminobenzoyl)-3'-(N-methyl-N-acetylaminomethyl)-4-aza-[6,4]-spiro-[5,6]-benzoundec-2'-ene (Compound 5)

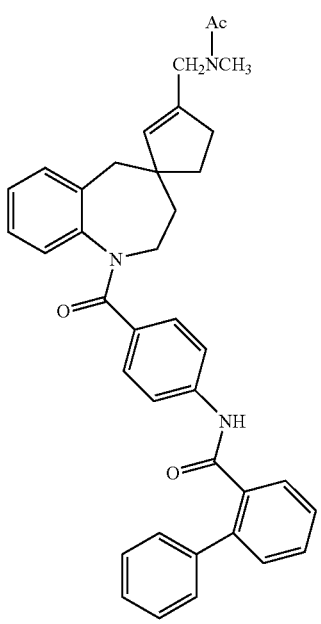

To a solution of the amine (Example 16) (10 mg) and triethyl amine (50 mg) in CH$_2$Cl$_2$ (5 mL) was added acetic anhydride (35 mg) at room temperature under nitrogen and stirred for 5 hours. Most of solvent was removed in vacuo and the residue was purified by column chromatography on silica gel (8 g, ethyl acetate/hexane 90:10) to give the title compound (9 mg) as white powder. MS (MH$^+$=584).

EXAMPLE 18

4-(2-Phenylbenzoyl-4-aminobenzoyl)-3'(carboxyl)-4-aza-[6,4]-spiro-[5,6]-benzoundec-2'-ene (Compound 4)

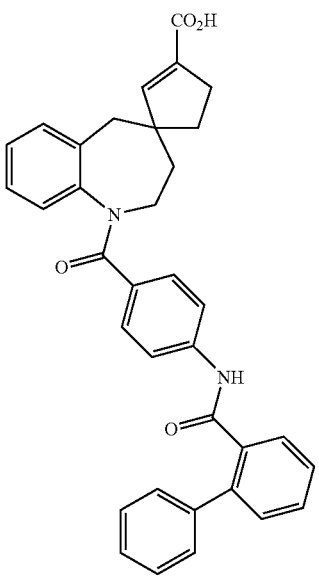

Using 4-(4-aminobenzoyl)-3'-(carbomethoxy)-4-aza-[6,4]-spiro-[5,6]-benzoundec-2'-ene (title compound of example 9) as a starting compound in the procedure analogous to that of Examples 10 and 11 gives the title compound as white powder. MS(MH+=543).

EXAMPLE 19

4-(2-Fluorobenzoyl-4-aminobenzoyl)-4-aza-[6,5]-spiro-[5,6]-benzododec-2'-ene (Compound 101)

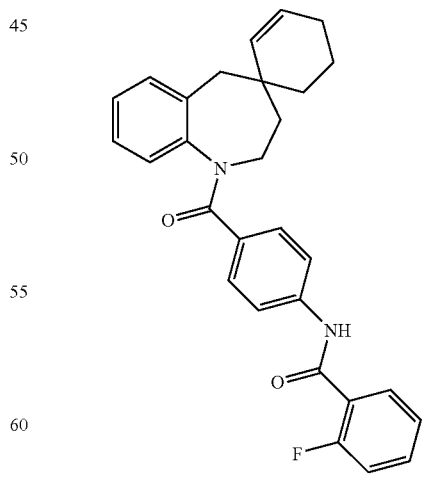

The procedure of Example 6 was followed except that 4-nitrobenzoyl chloride was substituted with 4-(2-fluorobenzoylamido)benzoyl chloride, and the title compound was obtained as white powder. MS (MH$^+$=455).

EXAMPLE 20

4-(2-Fluorobenzoyl-4-aminobenzoyl)-3'-(carboxyl)-4-aza-[6,4]-spiro-[5,6]-benzoundec-2'-ene (Compound 20)

To a solution of 4-(4-aminobenzoyl)-3'-(carbomethoxy)-4-aza-[6,4]-spiro-[5,6]-benzoundec-2'-ene (Example 9) was added $Et_3N$ in $CH_2Cl_2$ and a solution of 2-fluorobenzoyl chloride at 0° C. under nitrogen during 15 min. period. After addition, the mixture was allowed to warm to room temperature and stirred for another hour. The mixture was poured into cold 1 N NaOH (100 mL). The organic layer was separated and the aqueous was extracted with $CH_2Cl_2$ (2×100 mL). The combined organic layer was dried ($Na_2SO_4$) and the solvent was removed in vacuo. The oily residue was purified by column chromatography on silica gel to give 4-(2-fluorobenzoyl-4-aminobenzoyl)-3'(carbomethoxy)-4-aza-[6,4]-spiro-[5,6]-benzoundec-2'-ene.

Analogous to the procedure of Example 11, a mixture of 4-(2-fluorobenzoyl-4-aminobenzoyl)-3'(carbomethoxy)-4-aza-[6,4]-spiro-[5,6]-benzoundec-2'-ene was stirred in methanol (150 mL) and 1 N NaOH (50 mL) at room temperature under nitrogen for 16 hr. Most of methanol was removed in vacuo and the residue was diluted with water and ether. The aqueous layer was separated and the organic layer was extracted with 0.5 N NaOH (50 mL). The combined aqueous layer was cooled to 0° C. and acidified to pH=1 with conc. HCl. This was extracted with $CH_2Cl_2$ (3×100 mL). The combined organic layer was dried ($Na_2SO_4$) and solvent was removed in vacuo to give the title compound as an off-white powder. MS ($MH^+$=485).

EXAMPLE 21

4-(2-Fluorobenzoyl-4-aminobenzoyl)-3'-[2-(N,N-dimethylaminoethylcarbonyl)]-4-aza-[6,4]-spiro-[5,6]-benzoundec-2'-ene (Compound 16)

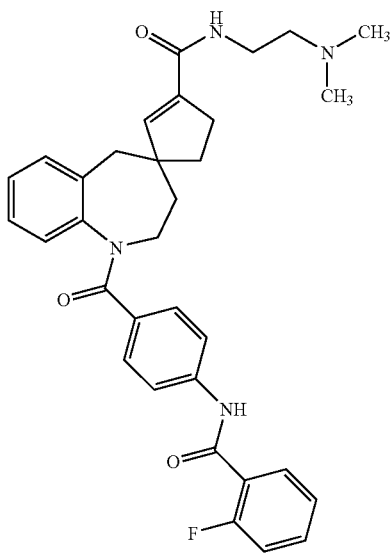

The procedure of Example 12 was followed except that the acid of Example 11 was substituted with 4-(2-Fluorobenzoyl-4-aminobenzoyl)-3'-(carboxyl)-4-aza-[6,4]-spiro-[5,6]-benzoundec-2'-ene of Example 20, and the title compound was obtained as white powder. MS ($MH^+$=555).

EXAMPLE 22

4-Aza-2'-hydroxy-[6,5]-spiro-[5,6]-benzododecane

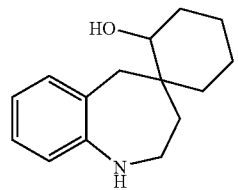

To a solution of 3-oxo-4-aza-[6,5]-spiro-[5,6]-benzododec-2'-ene (1.0 g) in THF (100 mL) was added a solution of $BH_3$-THF in THF (1 M, 4.3 mL) at −78° C. under $N_2$. After addition, the mixture was allowed to warm to room temperature and stirred for 16 hours. The resulting mixture was cooled to 0° C. and 6 N NaOH (10 mL) was added followed by 30% $H_2O_2$ (5 mL) and stirred for 3 hours. Most of THF was removed in vacuo and the residue was treated with buffer solution (PH=4, 150 mL). This was extracted with $CH_2Cl_2$ (1×250 mL, 2×100 mL). The combined organic layer was dried ($Na_2SO_4$) and the solvent was removed in vacuo. The oily residue was purified by column chromatography on silica gel (300 g, EtOAc/hexane 3:7) to give the title compound (two isomers) as a thick yellow oil (510 mg). MS ($MH^+$=232)

EXAMPLE 23

4-Aza-2'-oxo-[6,5]-spiro-[5,6]-benzododecane

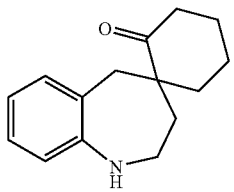

To a solution of $CrO_3$ (350 mg), conc $H_2SO_4$ (0.5 mL), in $H_2O$ (3 mL) and acetone (25 mL) was added a solution of 4-aza-2'-hydroxy-[6,5]-spiro-[5,6]-benzododec-2'-ene (500 mg) at 0° C. and stirred for 1 hour. The resulting mixture was diluted with water (25 mL) and most of acetone was removed in vacuo. This was made basic with saturated $NaHCO_3$. This was extracted with $CH_2Cl_2$ (3×100 mL) and the combined organic layer was dried ($Na_2SO_4$). The solvent was removed in vacuo to give the title compound as a thick pale yellow oil (315 mg). MS ($MH^+$=230).

EXAMPLE 24

4-(2-Phenylbenzoyl-4-aminobenzoyl)-4-aza-2'-oxo-[6,5]-spiro-[5,6]-benzododecane (Compound 30)

To a solution of 4-aza-2'-oxo-[6,5]-spiro-[5,6]-benzododecane (Example 23) was added Et$_3$N in CH$_2$Cl$_2$ and a solution of 4-(2-phenylbenzoyl-4-aminobenzoyl) chloride in CH$_2$Cl$_2$ (50 mL) dropwise at room temperature under N$_2$ and the resulting mixture was stirred for 16 hr. This was poured into cold 1 N NaOH (100 mL) and the organic layer was separated and the aqueous layer was extracted with CH$_2$Cl$_2$ (2×100 mL). The combined organic layer was dried (Na$_2$SO$_4$). The solvent was removed in vacuo to give the title compound as a pale yellow solid. The title compound was obtained as colorless solid. MS (MH$^+$=529).

EXAMPLE 25

4-(4-Carbomethoxybenzoyl)-4-aza-[6,5]-spiro-[5,6]-benzododec-2'-ene (Compound 54)

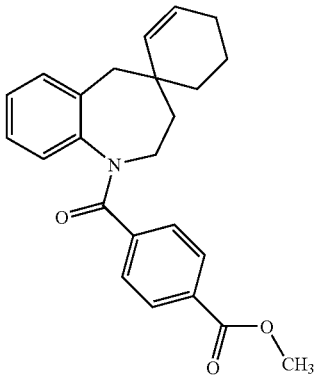

The procedure of Example 6 was followed except that 4-nitrobenzoyl chloride was substituted with 4-carbomethoxybenzoyl chloride, and the title compound was obtained as colorless solid. MS (MH$^+$=376).

EXAMPLE 26

4-(4-Carboxybenzoyl)-4-aza-[6,5]-spiro-[5,6]-benzododec-2'-ene (Compound 65)

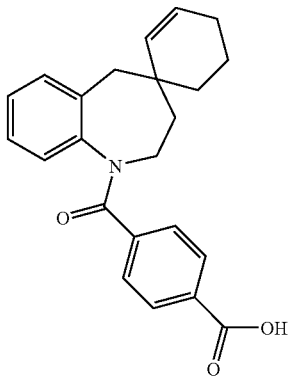

A mixture of 4-(4-carbomethoxybenzoyl)-4-aza-[6,5]-spiro-[5,6]-benzododec-2'-ene (52 mg), 1 N NaOH (1 mL), THF (9 mL) was heated to reflux for 16 hours. The mixture was allowed to cool to room temperature and most of THF was removed in vacuo. The mixture was acidified to PH=1 with conc. HCl and then extracted with CH$_2$Cl$_2$ (3×10 mL). The combined organic layer was dried (Na$_2$SO$_4$) and the solvent was removed in vacuo to give the title compound as white powder (45 mg). MS (MH$^+$=362).

EXAMPLE 27

4-(4-Anilinocarbonylbenzoyl)-4-aza-[6,5]-spiro-[5,6]-benzododec-2'-ene (Compound 27)

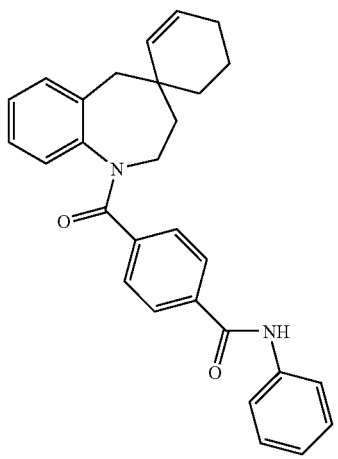

4-(4-Chlorocarbonyl(benzoyl)-4-aza-[6,5]-spiro-[5,6]-benzododec-2'-ene was prepared from 4-(4-carboxybenzoyl)-4-aza-[6,5]-spiro-[5,6]-benzododec-2'-ene (45 mg) and SOCl$_2$ (91 mg). The freshly prepared acid chloride was treated with CH$_2$Cl$_2$ (30 mL) and Et$_3$N (100 mg) followed by aniline (35 mg). The resulting mixture was stirred for 2 hours and the solvent was removed in vacuo. The residue was purified by column chromatography on silica gel (30 g, EtOAc/Hexane 1:4~1:3) to give the title compound as light brown solid (53 mg). MS (MH$^+$=437)

EXAMPLE 28

4-Aza-[6,5]-spiro-[5,6]-benzododec-2'-ene

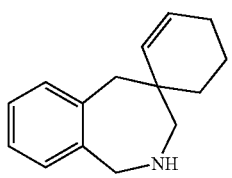

The procedure of Example 5 was followed except that 4-aza-3-oxo[6,5]-spiro-[5,6]-benzododec-2'-ene was substituted with 3-aza-4-oxo[6,5]-spiro-[5,6]-benzododec-2'-ene, and the title compound was obtained as pale yellow oil. MS (MH$^+$=214).

EXAMPLE 29

4-(2-Fluorobenzoyl-4-aminobenzoyl)-3-aza-[6,5]-spiro-[5,6]-benzododec-2'-ene (Compound 128)

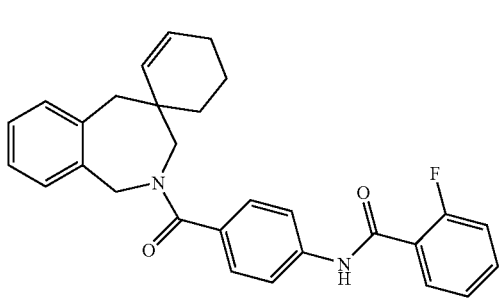

The procedure of Example 19 was followed except that 4-aza-[6,5]-spiro-[5,6]-benzododec-2'-ene was substituted with 3-aza-[6,5]-spiro-[5,6]-benzododec-2'-ene, and the title compound was obtained as white powder. MS (MH$^+$=455).

EXAMPLE 30

4-(2-Methoxy-4-nitrobenzoyl)-4-aza-[6,5]-spiro-[5,6]-benzododec-2'-ene

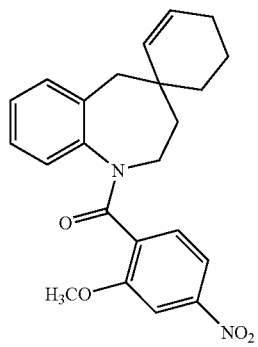

The procedure of Example 6 was followed, but 4-nitrobenzoyl chloride was substituted with 2-methoxy-4-nitrobenzoyl chloride. The title compound was obtained as yellow solid. MS(MH+)=393.

EXAMPLE 31

4-(4-Ethoxycarboyloxy-3,5-dimethoxybenzoyl)-4-aza-[6,5]-spiro-[5,6]-benzododec-2'-ene (Compound 206)

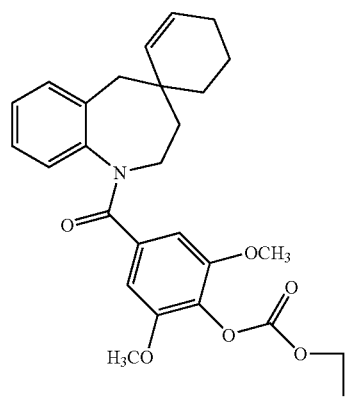

The procedure of Example 6 was followed but 4-nitrobenzoyl chloride was substituted with 4-ethoxycarboyloxy-3,5-dimethoxybenzoyl chloride. The title compound was obtained as yellow solid. MS(MH+)=466

EXAMPLE 32

4-(3-Methoxy-4-nitrobenzoyl)-4-aza-[6,5]-spiro-[5,6]-benzododec-2'-ene

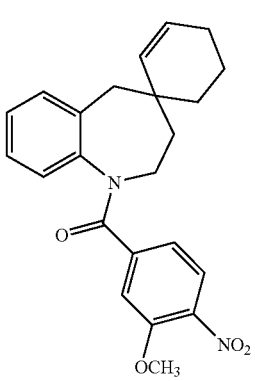

The procedure of Example 6 was followed but 4-nitrobenzoyl chloride was substituted with 3-methoxy-4-nitrobenzoyl chloride. The title compound was obtained as yellow solid. MS(MH+)=393.

EXAMPLE 33

4-(4-Amino-3-methoxybenzoyl)-4-aza-[6,5]-spiro-[5,6]-benzododec-2'-ene

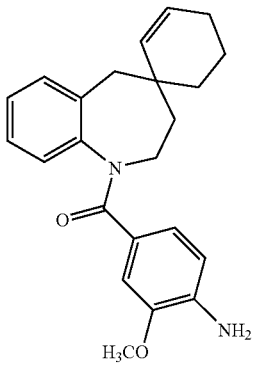

A mixture of 4-(3-methoxy-4-nitrobenzoyl)-4-aza-[6,5]-spiro-[5,6]-benzododec-2'-ene and $SnCl_2$ in ethanol was heated to reflux under $N_2$ for 12 h. The mixture was allowed to cool to room temperature and saturated $NaHCO_3$ was added. This was filtered through a pad of Celite and washed with several portions of $CH_2Cl_2$. The combined filtrate was conc. in vacuo to give the title compound. MS(MH+)=363.

EXAMPLE 34

4-(3-Methoxy-4-(pyrrol-1-yl-3-carboxaldehyde)benzoyl)-4-aza-[6,5]-spiro-[5,6]-benzododec-2'-ene (Compound 167)

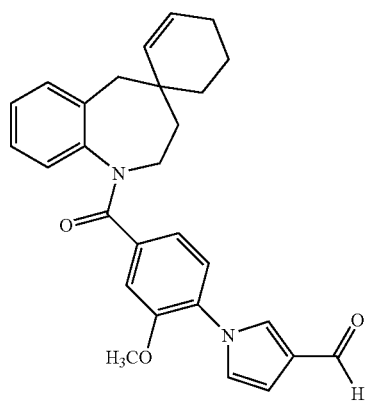

A solution of 4-(4-amino-3-methoxybenzoyl)-4-aza-[6,5]-spiro-[5,6]-benzododec-2'-ene (120 mg, 0.33 mmol) and 2,5-dimethoxy-3-tetrahydrofurancarboxaldehyde (300 mg) in acetic acid (5 mL) was refluxed for 2 h. The solution was cooled and the solvent was removed under high vacuum with toluene as an azeotrope agent. The residue was chromatographed on silica gel to yield the title compound as a light yellow solid. MS(M+)=441.

EXAMPLE 35

4-[3-Methoxy-4-(3-hydroxymethylpyrrol-1-yl)benzoyl]-4-aza-[6,5]-spiro-[5,6]-benzododec-2'-ene (Compound 178)

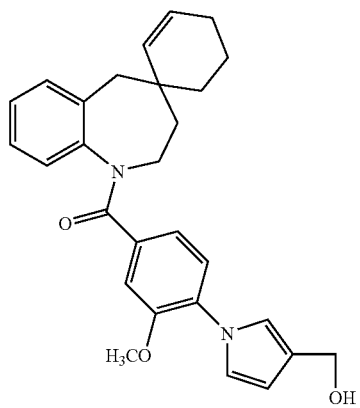

To a solution of 4-(3-methoxy-4-(pyrrol-1-yl-3-carboxaldehyde)benzoyl)-4-aza-[6,5]-spiro-[5,6]-benzododec-2'-ene (100 mg, 0.23 mmol) in methanol (25 mL) at room temperature, $NaBH_4$ was added. The mixture stirred for 3 h. The resulting crude was treated with 1 N NaOH (20 mL) and stirred for 15 min, then diluted with $H_2O$ and $CH_2Cl_2$. The organic layer was separated and the aqueous layer was extracted with $CH_2Cl_2$ (2×50 mL). The combined organic layer was dried ($Na_2SO_4$) and the solvent was removed in vacuo to give the title compound as a white powder. MS(MH+)=443.

EXAMPLE 36

4-(3-Methoxy-4-nitrobenzoyl)-4-aza-3'-formyl-[6,4]-spiro-[5,6]-benzoundec-2'-ene

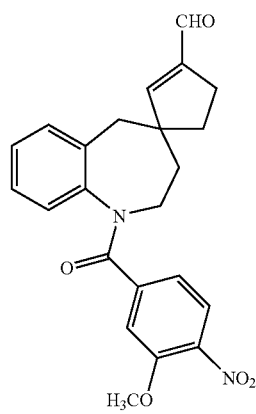

A solution of 4-(3-methoxy-4-nitrobenzoyl)-4-aza-[6,5]-spiro-[5,6]-benzododec-2'-ene in $CH_2Cl_2$ at −78° C. was treated with ozone. The excess of ozone was removed with a stream of nitrogen and the resulting mixture was treated with methyl sulfide followed by toluene sulfonic acid monohydrate (TsOH—$H_2O$). The mixture was allowed to warm to room temperature and stirred for 48 h. The mixture was poured into cold 1 N NaOH (100 mL) and the organic layer was separated. The aqueous layer was extracted with methylene chloride (2×100 mL). The combined organic was dried (Na$_2$SO$_4$) and the solvent was removed in vacuo. The oily residue was purified by column chromatography on silica gel to yield the title compound as yellow crystals. MS(MH+)=407.

EXAMPLE 37

4-(3-Methoxy-4-nitrobenzoyl)-4-aza-3'-carboxy-[6,4]-spiro-[5,6]-benzoundec-2'-ene

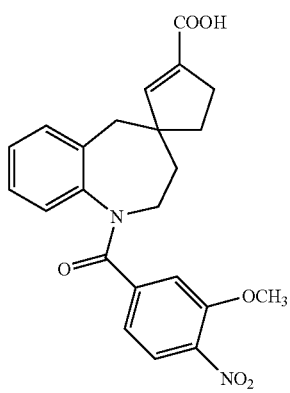

To a solution of CrO$_3$, conc. H$_2$SO$_4$ in H$_2$O and acetone was added a solution of 4-(3-methoxy-4-nitrobenzoyl)-4-aza-3'-formyl-[6,4]-spiro-[5,6]-benzoundec-2'-ene in acetone at 0° C. during 1 h period. After addition, the mixture was treated with water and the organic layer was separated. The aqueous layer was extracted with CH$_2$Cl$_2$ (2×200 mL). The combined organic layer was dried (Na$_2$SO$_4$) and the solvent was removed in vacuo to yield the title compound. MS(M+1)=423.

EXAMPLE 38

4-(3-Methoxy-4-nitrobenzoyl)-4-aza-3'-[2-(N,N-dimethylamino)ethylcarboxamido]-[6,4]-spiro-[5,6] benzoundec-2'-ene (Compound 186)

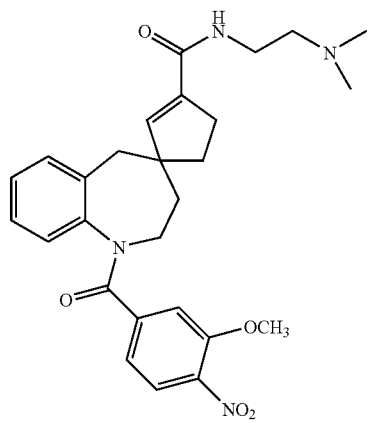

4-(3-Methoxy-4-nitrobenzoyl)-4-aza-3'-carboxy-[6,4]-spiro-[5,6]-benzoundec-2'-ene (500 mg, 1.2 mmol) in CH$_2$Cl$_2$ was stirred at room temperature. N,N-Dimethylethylenediamine (417 mg) and triethylamine (396 mg) were added, then 1-hydroxybenzotriazole(350 mg) was added. The mixture was cooled to 0° C. and 1-(3-dimethylaminopropyl)-3-ethylcarbodiimide (270 mg) was added in one portion. The resulting mixture stirred for 5 h at room temp. The mixture was cooled to 0° C., 0.5 N aq HCl (15 ml) was added and the mixture was stirred for 30 min. The organic layer was separated and washed with aq NaCl, the aqueous layer was extracted with CH$_2$Cl$_2$ (3×200 mL). The combined organic layer was dried (Na$_2$SO$_4$) and the solvent was removed in vacuo. The oily residue was chromatographed on silica gel to yield the title compound as an off-white powder. MS(MH$^+$)=493

EXAMPLE 39

4-(4-Amino-3-methoxybenzoyl)-4-aza-3'-[2-(N,N-dimethylamino)ethylcarboxamido]-[6,4]-spiro-[5,6]-benzoundec-2'-ene (Compound 187)

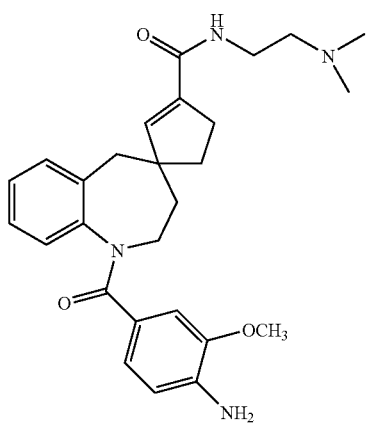

A mixture of 4-(3-methoxy-4-nitrobenzoyl)-4-aza-3'-[2-(N,N-dimethylamino)ethylcarboxamido)]-[6,4]-spiro-[5,6]-benzoundec-2'-ene and SnCl$_2$ in ethanol was heated to reflux under N$_2$ for 12 h. The mixture was cooled to room temperature and saturated aq NaHCO$_3$ was added. This was filtered through a pad of Celite and washed with several portions of CH$_2$Cl$_2$. The combined filtrate was conc. in vacuo to yield the title compound. MS(MH+)=463.

EXAMPLE 40

4-[3-Methoxy-4-(pyrrol-1-yl-3-carboxaldehyde)benzoyl]-3'-[2-(N,N-dimethylamino)ethylcarboxamido]-4-aza-[6,4]-spiro-[5,6]-benzoundec-2'-ene (Compound 189)

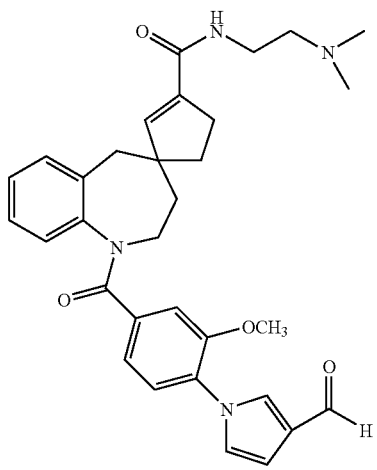

A solution of 4-(4-amino-3-methoxybenzoyl)-4-aza-3'-[2-(N,N-dimethylamino)ethylcarboxamido]-[6,4]-spiro-[5,6]-benzoundec-2'-ene (120 mg, 0.331 mmol) and 2,5-dimethoxyl-3-tetrahydrofurancarboxaldehyde (300 mg) in acetic acid (5 mL) was refluxed for 2 h. The solution was cooled and solvent removed under high vacuum with toluene as an azeotrope agent. The residue was chromatographed on silica gel to yield the title compound as a light yellow solid. MS(M+)=541

EXAMPLE 41

4-[3-Methoxy-4-(3-hydroxymethylpyrrol-1-yl)benzoyl]-3'-[2-(N,N-dimethylamino)ethylcarboxamido]-4-aza-[6,4]-spiro-[5,6]-benzoundec-2'-ene (Compound 190)

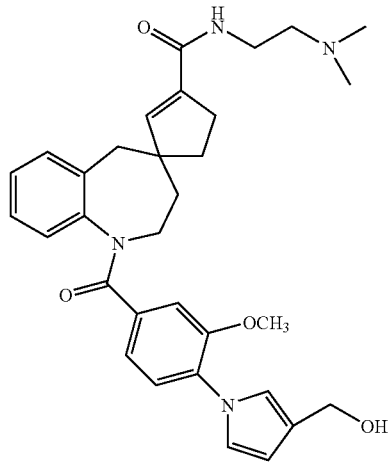

4-[3-Methoxy-4-(pyrrol-1-yl-3-carboxaldehyde)benzoyl]-3'-[2-(N,N-dimethylamino)ethylcarboxamido]-4-aza-[6,4]-spiro-[5,6]-benzoundec-2'-ene (75 mg, 0.139 mmol) was suspended in 25 mL methanol and 10 mg of NaBH$_4$ was added at room temperature. The mixture was stirred under N$_2$ for 4 h. The mixture was treated with 20 mL of 1 N NaOH and stirred for 15 min then diluted with H$_2$O and CH$_2$Cl$_2$. The organic layer was separated and the aqueous layer was extracted with CH$_2$Cl$_2$ (2×50 mL). The combined organic layer was dried (Na$_2$SO$_4$) and the solvent was removed in vacuo to give the title compound as white powder. MS(MH+)=543.

EXAMPLE 42

Separation of the enantiomers of 4-[3-methoxy-4-(3-hydroxymethylpyrrol-1-yl)benzoyl]-3'-[2-(N,N-dimethylamino)ethylcarboxamido]-4-aza-[6,4]-spiro-[5,6]-benzoundec-2'-ene (Compound 197)

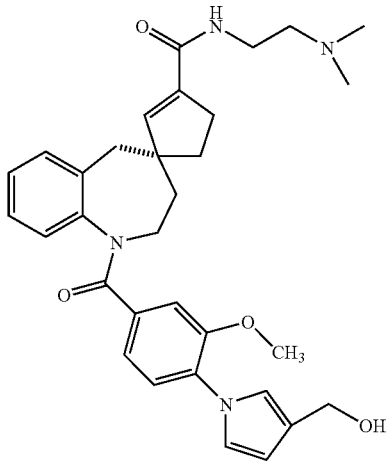

(Compound 198)

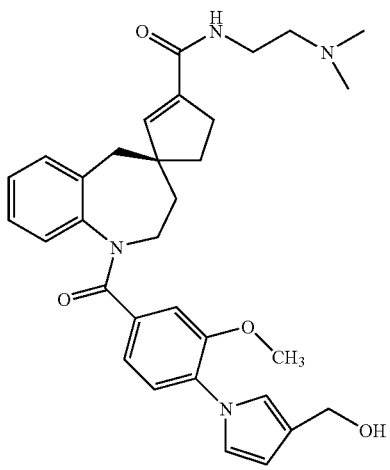

Racemic 4-[3-methoxy-4-(3-hydroxymethylpyrrol-1-yl)benzoyl]-3'-[2-(N,N-dimethylamino)ethylcarboxamido]-4-aza-[6,4]-spiro-[5,6]-benzoundec-2'-ene was separated by Chiral HPLC. Each enantiomer gave the same MS(MH+)=543.

EXAMPLE 43

4-(4-Hydroxybenzoyl)-4-aza-[6,5]-spiro-[5,6]-benzododec-2'-ene

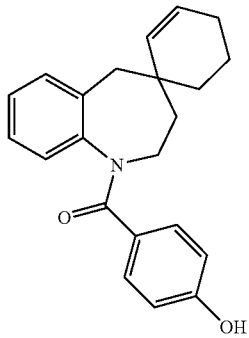

The procedure of Example-6 was followed but 4-nitrobenzoyl chloride was substituted by 4-acetoxybenzoyl chloride. The title compound was obtained as white solid. MS(MH+)=334.

EXAMPLE 44

4-(4-(Piperidin-4-yloxy)benzoyl)-4-aza-[6,5]-spiro-[5,6]-benzododec-2'-ene

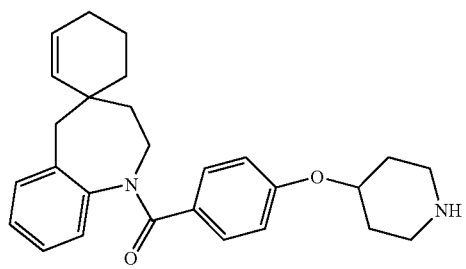

To a solution of tert-butyl-4-hydroxy-1-piperidinecarboxylate (310 mg, 1.5 mmol) and 4-(4-hydroxybenzoyl)-4-aza-[6,5]-spiro-[5,6]-benzododec-2'-ene (410 mg, 0.12 mmol) in THF (100 mL), diethyl azodicarboxylate (322 mg, 1.9 mmol) was added and stirring continued for 30 min. Triphenylphosphine (483 mg) was added and stirring continued for 6 h. The crude product was treated with water (100 mL) and diluted with EtOAc. The organic layer was separated and the aqueous layer was extracted with $CH_2Cl_2$ (2×50 mL). The combined organic layer was dried ($Na_2SO_4$) and the solvent was removed in vacuo. The concentrated sample was treated with $CF_3COOH/CH_2Cl_2$(1:10) and stirred for 4 h. The solvent was removed in vacuo. The mixture was diluted with $CH_2Cl_2$ and washed with $NaHCO_3$, the organic layer was dried ($Na_2SO_4$) and concentrated in vacuo. The sample was purified by Chromatography on silica gel to give the title compound. MS(M+1)= 417.

EXAMPLE 45

4-(4-(N-acetylpiperidin-4-yloxy)benzoyl)-4-aza-[6,5]-spiro-[5,6]-benzododec-2'-ene (Compound 224)

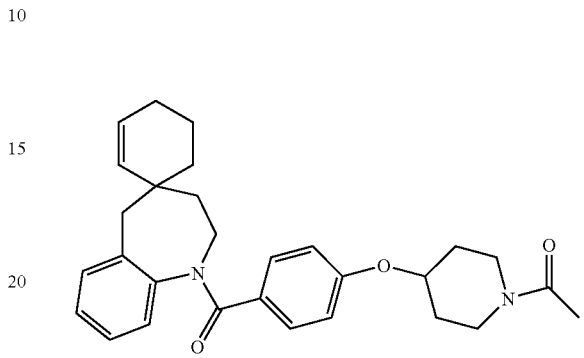

To a solution of 4-(4-(piperidin-4-yloxy)benzoyl)-4-aza-[6,5]-spiro-[5,6]-benzododec-2'-ene (40 mg) and triethylamine (20 mg) in $CH_2Cl_2$ (10 mL), at room temperature under $N_2$ was added acetic anhydride (35 mg). The mixture was stirred for 5 h. Most of solvent was removed in vacuo and the residue was chromatographed on silica gel to yield the title compound as a white powder. MS(MH+)=459.

EXAMPLE 46

4-(3-Fluoro-4-(pyrazol-1-yl)benzoyl)-4-aza-[6,5]-spiro-[5,6]-benzododec-2'-ene (Compound 156)

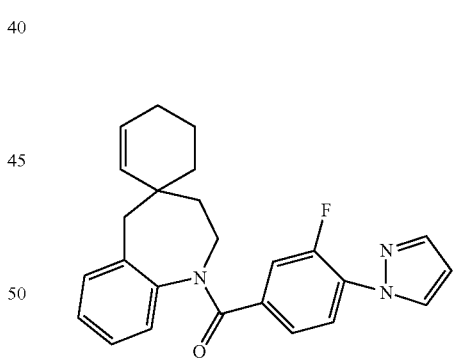

4-(3,4-Difluorobenzoyl)-4-aza-[6,5]-spiro-[5,6]-benzododec-2'-ene (200 mg, 0.57 mmol) was dissolved in THF (85 mL). Sodium hydride (58 mg of 60% in oil, 0.85 mmol) and pyrazole (91.8 mg, 1.1 mmol) were added and the mixture was heated to 50° C. for 16 h. The solution was cooled and treated with 10 mL aq sat ammonium chloride. The mixture was diluted with ethyl acetate and washed with water(3×). The organic layer was dried ($Na_2SO_4$) and concentrated in vacuo to give a dark brown solid. Chromatography on silica gel yielded the title compound. MS(MH+)= 402.

EXAMPLE 47

4-(3-Fluoro-4-(piperidin-4-yloxy)benzoyl)-4-aza-[6,5]-spiro-[5,6]-benzododec-2'-ene

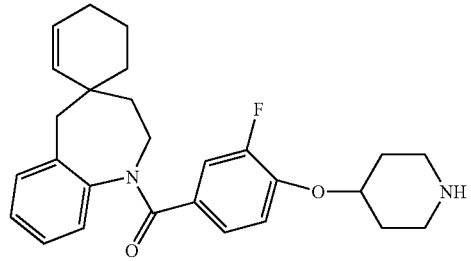

4-(3,4-Difluorobenzoyl)-4-aza-[6,5]-spiro-[5,6]-benzododec-2'-ene (200 mg, 0.57 mmol) was dissolved in THF (85 mL). Sodium hydride (58 mg of 60% in oil, 0.85 mmol) was added followed by tert-butyl-4-hydroxy-1-piperidinecarboxylate, and the mixture was stirred at 80° C. for 16 h. The solution was cooled and treated with 10 mL sat aq ammonium chloride. The mixture was diluted with ethyl acetate and washed with water (2×), the organic layer was dried ($Na_2SO_4$) and concentrated in vacuo to give a yellow solid. The sample was treated with $CF_3COOH/CH_2Cl_2$(1:10) and stirred for 4 h. The solvent was removed in vacuo. The mixture was diluted with $CH_2Cl_2$ and washed with $NaHCO_3$, the organic layer was dried ($Na_2SO_4$) and concentrated in vacuo. The sample was purified by Chromatography on silica gel to give the title compound. MS(MH+)= 435.

EXAMPLE 48

4-(3-Fluoro-4-(N-acetylpiperidin-4-yloxy)benzoyl)-4-aza-[6,5]-spiro-[5,6]-benzododec-2'-ene (Compound 168)

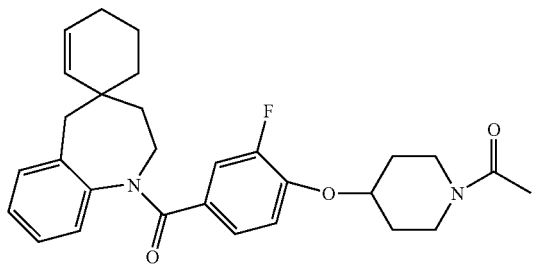

The procedure Example 45 was followed except using the starting material 4-(3-fluoro-4-(piperidin-4-yloxy)benzoyl)-4-aza-[6,5]-spiro-[5,6]-benzododec-2'-ene. The title compound was obtained as a white powder. MS(MH+)=477.

EXAMPLE 49

(A) In-Vitro Binding Assay

Assay buffer is 50 mM Tris-Cl, 5 mM $MgCl_2$, 0.1% BSA (pH 7.5) containing 5 µg/ml of aprotinin, leupeptin, pepstatin, 50 µg/ml bacitracin, and 1 mM Pefabloc. H3 vasopressin is $^3$H-arginine-8-vasopressin (68.5 Ci/mmol, final concentration in assay is 0.65-0.75 nM). Into wells of 96-well round bottom polypropylene plates are added buffer, test compound, membrane (containing human V2 receptor), and H3 vasopressin. The reaction plates are allowed to sit at room temperature for one hour. The samples are filtered through Unifilter GF/C plates (presoaked in 0.3 polyethyleneimine). The plates are washed 5 times with cold physiological saline containing 0.05% Tween 20. After drying, the bottom of the filter plates are sealed and 0.025 ml of Microscint-20 is added to each filter. The top of the plate is sealed, and the plate is counted. Non-specific binding is determined by the addition of 1.25 µM arginine-8-vasopressin in those wells. % Inh. is calculated as follows:

$$\% \text{ inhibition} = 100 - 100 \times \frac{\text{peak response after drug}}{\text{peak response before drug}}$$

(B) V1a Vasopressin Receptor Functional Activity

The V1a receptor is a G-protein coupled receptor, which upon activation triggers an increase in intracellular calcium mobilization. To evaluate compounds for their functional V1a receptor activity, HEK-293 cells were transfected with the human V1a receptor (V1a-HEK cells). HEK-293 cells were grown in DMEM (Dulbecco's modified Eagle Media) supplemented with 10% FBS and glutamine. HEK-cells were passed biweekly by trypsinization and seeded into 96 well plates at 33,000 cells per well. HEK-293 cells were transfected with human V1a receptor DNA using DMRIE-C reagent from Life Technologies. Stable lines were generated by selecting cells grown in culture media containing geneticin. After growing in Packard Clear-View black 96 well plates for 4-6 days, V1a-HEK cells were loaded with the calcium-sensitive fluorescence dye, FLUO-3 AM. Changes in cell fluorescence were quantitated using FLIPR (Fluorometric Imaging Plate Reader; Molecular Devices, Sunnyvale, Calif.). Test compounds were first added to the cells and the resulting changes in fluorescence measured to detect receptor agonistic activity. Five minutes later the cells were challenged with vasopressin to test compounds for their antagonistic activity. Receptor antagonists inhibit the ability of vasopressin to stimulate increases in intracellular fluorescence. $IC_{50}$'s were calculated.

Tables I through VI below set forth the vasopressin receptor binding data and V1a vasopressin Receptor functional activity of some compounds of the instant invention.

TABLE I

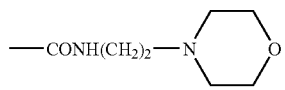

| Cpd No. | R⁵ | R⁶ | R⁷ | R⁸ | V1a Functional Activity (IC₅₀ in μM) | Receptor Binding (IC₅₀ in μM or % Inh. @ concentration in μM) V1a | V1b | V2 |
|---|---|---|---|---|---|---|---|---|
| 1 | —CH₂OH | H | Ph | H | <0.01 | 0.009 | | 0.018 |
| 2 | —CHO | H | Ph | H | | 0.016 | | 0.029 |
| 3 | —CH₂NHCH₃ | H | Ph | H | <0.01 | 0.009 | | 0.018 |
| 4 | —CO₂H | H | Ph | H | 0.02 | 0.037 | | 0.014 |
| 5 | —CH₂NCH₃Ac | H | Ph | H | <0.01 | 0.020 | | 0.022 |
| 6 | —CONH(CH₂)₂CH | H | Ph | H | 0.005 | 0.006 | | 0.011 |
| 7 | —CO₂H | H | F | H | | 43% @ 0.1 | | 15% @ 0.1 |
| 8 | —CONH(CH₂)₂CH | H | F | H | 0.099 | 0.004 | | 41% @ 0.1 |
| 9 | —CONH(CH₂)₂N(CH₃)₂ | H | Ph | H | 0.004 | 0.005 | 12% @ 10 | 0.011 |
| 10 | —CONHCH₂CO₂H | H | Ph | H | | 0.024 | | 0.018 |
| 11 | —CONH(CH₂)₂OH | Cl | CH₃ | F | | 0.028 | | 0.010 |
| 12 | —CONHCH₂CO₂CH₃ | H | Ph | H | | 0.013 | | 0.018 |
| 13 | —CONH(CH₂)₂N(CH₃)₂ | H | CH₃ | F | 0.07 | 0.005 | | 0.018 |
| 14 | —CONH(CH₂)₃N(CH₃)₂ | H | CH₃ | F | 0.059 | 0.005 | | 0.023 |
| 15 | —CH₂NHCH₂CO₂CH₃ | H | CH₃ | F | 0.135 | 0.007 | | 0.100 |
| 16 | —CONH(CH₂)₂N(CH₃)₂ | H | F | H | 0.126 | 0.008 | 8% @ 10 | 17% @ 0.1 |
| 17 | —CONH(CH₂)₂—N(morpholine) | H | F | H | 0.227 | 0.014 | | 18% @ 0.1 |
| 18 | —CONH(CH₂)₂—N(piperidine) | H | F | H | 0.95 | 0.007 | | 23% @ 0.1 |
| 19 | —CONH(CH₂)₂—N(pyrrolidine) | H | F | H | 0.155 | 0.008 | | 22% @ 0.1 |
| 20[1] | —CONH(CH₂)₂N(CH₃)₂ | H | Ph | H | 0.002 | 0.003 | 13% @ 10 | 0.016 |
| 21 | —CONH(CH₂)₂N(CH₃)₂ | H | Ph | H | 0.008 | 0.181 | 7% @ 10 | 0.440 |
| 22 | —CONH(CH₂)₂N(CH₃)₂ | H | F | H | | 0.003 | 17% @ 10 | 15% @ 0.1 |
| 23 | —CONH(CH₂)₂N(CH₃)₂ | H | F | H | 15% @ 0.1 | 13.73 | | 1% @ 0.1 |

[1]Enantiomer (determination of absolute stereochemistry pending)

TABLE II

| Compound No. | $R_9$ | $R_{10}$ | $R_{11}$ | V1a Functional Activity ($IC_{50}$ in μM) | V1a Receptor Binding ($IC_{50}$ in μM or % Inh. @ Concentration in μM) | |
|---|---|---|---|---|---|---|
| | | | | | V1a | V2 |
| 24 | H | H | —CN | | 0.800 | 26% @ 10 |
| 25 | H | H | —NH$_2$ | | 10 | 7% @ 10 |
| 26 | H | H | —NHC$_2$H$_5$ | 0.105 | 0.160 | 10 |
| 27 | H | H | —NHCOPh(2-Ph) | 0.008 | 0.100 | 0.270 |
| 28 | H | H | —NHCOPh(2-CH$_3$) | | 0.250 | 1% @ 10 |
| 29 | O | | —OCH$_3$ | | 0.013 | 8% @ 1 |
| 30 | O | | —NHCOPh(2-Ph) | | 0.035 | 0.033 |
| 31 | O | | —NHCOPh(2-CH$_3$) | | 0.021 | 0.054 |
| 32 | OH | H | —NHCOPh(2-Ph) | | 0.061 | 0.028 |

TABLE III

| Compound No. | Y | Q | r | $R_1$ | $R_{12}$ | V1a Functional Activity ($IC_{50}$ in μM) | Receptor Binding ($IC_{50}$ in μM or % Inh. @ concentration in μM) | |
|---|---|---|---|---|---|---|---|---|
| | | | | | | | V1a | V2 |
| 33 | CH | C | 0 | H | 4-CN | >1 | 0.130 | 25 |
| 34 | CH | CH | 0 | H | H | | 0.65 | 25 |
| 35 | CH | N | 0 | H | H | | 1.4 | >25 |
| 36 | CH | C | 0 | 5-F | 4-CN | | 0.44 | 28%@10 |
| 37 | CH | C | 0 | H | 4-OCH$_3$ | 0.096 | 0.11 | 37%@10 |
| 38 | CH | C | 0 | H | 4-CF$_3$ | | 1.6 | 35%@10 |
| 39 | CH | C | 0 | H | 4-Cl | | 1.1 | 10 |
| 40 | CH | C | 0 | H | 4-I | | 0.57 | 27%@10 |
| 41 | CH | C | 0 | H | 4-CH$_3$ | | 0.32 | 0%@10 |
| 42 | CH | C | 0 | H | 4-CH$_2$NH$_2$ | | 0% @10 | 24%@10 |
| 43 | CH | C | 0 | H | 3,4-di-F | | 0.68 | 42%@10 |
| 44 | CH | C | 0 | H | 4-F | | | 42%@10 |
| 45 | CH | C | 0 | H | 4-N(CH$_3$)$_2$ | | 0.1 | 10 |
| 46 | CH | CH | 0 | H | 3-Cl | | 3.5 | 33%@10 |
| 47 | CH | CH | 0 | H | 3,5-di-F | | 0.39 | 29%@10 |

TABLE III-continued

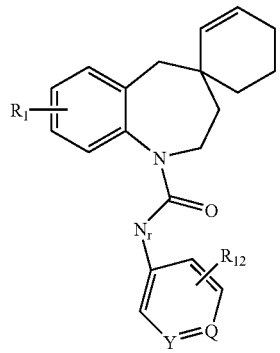

| Compound No. | Y | Q | r | $R_1$ | $R_{12}$ | V1a Functional Activity ($IC_{50}$ in μM) | Receptor Binding ($IC_{50}$ in μM or % Inh. @ concentration in μM) V1a | | V2 | |
|---|---|---|---|---|---|---|---|---|---|---|
| 48 | CH | C | 0 | H | 3,4-di-Cl | >1 | 33% | @10 | 16% | @10 |
| 49 | CH | C | 0 | H | 4-NO$_2$ | | 0.38 | | 30% | @10 |
| 50 | CH | CH | 0 | H | 3,5-di-CF$_3$ | | 20% | @10 | 26% | @10 |
| 51 | CH | CH | 0 | H | 3-Br | | 5.6 | | 33% | @10 |
| 52 | CH | CH | 0 | H | 3-CN | | 0.53 | | 28% | @10 |
| 53 | CH | C | 0 | H | 4-O(CH$_2$)$_3$CH$_3$ | 0.104 | 0.06 | | 8 | |
| 54 | CH | C | 0 | H | 4-CO$_2$CH$_3$ | 0.067 | 0.33 | | 10 | |
| 55 | CH | C | 0 | H | 4-CH$_2$NHCOPh | | 0% | @10 | 29% | @10 |
| 56 | CH | CH | 0 | H | 3-CF$_3$ | | 4.3 | | 0% | @10 |
| 57 | CH | C | 0 | H | 4-NHCOCH$_3$ | | 0.34 | | 4% | @ 1 |
| 58 | CH | C | 0 | 5-OCH$_3$ | 4-N(CH$_3$)$_2$ | | 28% | @ 1 | 4% | @ 1 |
| 59 | CH | C | 0 | 4-Cl | 4-N(CH$_3$)$_2$ | | 0.09 | | 24% | @ 1 |
| 60 | CH | C | 0 | H | 4-N(CH$_3$)$_2$ | | 0.051 | | 14% | @ 1 |
| 61 | CH | CH | 1 | H | H | | 11% | @ 1 | 3% | @ 1 |
| 62 | CH | C | 1 | H | 4-F | | 5% | @ 1 | 4% | @ 1 |
| 63 | CH | C | 0 | 5-OCH$_3$ | 4-CN | | 39% | @ 1 | 10% | @ 1 |
| 64 | CH | CH | 0 | H | 2-Ph | | 1% | @ 1 | 12% | @ 1 |
| 65 | CH | C | 0 | H | 4-CO$_2$H | | 8% | @ 1 | 11% | @ 1 |
| 66 | CH | C | 0 | H | 4-NHCO(2-Ph)Ph | 0.025 | 0.83 | | 0.19 | |
| 67 | CH | C | 0 | H | 4-NHCOPh | | 0.02 | | 0.39 | |
| 68 | CH | C | 0 | H | 4-NH$_2$ | | 0.81 | | 3% | @ 1 |
| 69 | CH | C | 0 | H | 4-NHCO(2-CH$_3$)Ph | 0.14 | 0.01 | | 0.07 | |
| 70 | CH | C | 0 | H | 4-NHCO(4-NH$_2$)Ph | | 0.01 | | 21% | @ 1 |
| 71 | CH | C | 0 | H | 4-NHCO(2-CH$_3$O)Ph | | 0.03 | | 0.20 | |
| 72 | CH | C | 0 | 4,5-di-Cl | 4-N(CH$_3$)$_2$ | | 0.04 | | 16% | @ 1 |
| 73 | CH | C | 0 | 4,5-di-Cl | 4-O(CH$_2$)$_3$CH$_3$ | | 0.09 | | 10% | @ 1 |
| 74 | CH | C | 0 | H | 2,4-di-(OCH$_3$) | | 0.19 | | 27% | @ 1 |
| 75 | CH | C | 0 | H | 3,4-di-(OCH$_3$) | | 0.07 | | 1% | @ 1 |
| 76 | CH | C | 0 | H | 4-O(CH$_2$)$_6$CH$_3$ | 1 | 0.9 | | 0% | @ 1 |
| 77 | CH | C | 0 | H | 4-OCF$_3$ | | 0.9 | | 16% | @ 1 |
| 78 | CH | C | 0 | H | 4-OH | | 0.51 | | 3% | @ 1 |
| 79 | CH | C | 0 | H | 4-NHCH(CH$_3$)$_2$ | | 0.19 | | 19% | @ 1 |
| 80 | CH | C | 0 | 5-Cl | 4-N(CH$_3$)$_2$ | | 0.05 | | 0.28 | |
| 81 | CH | C | 0 | H | 4-NHCO(3,4-diCH$_3$)Ph | | 0.14 | | 47% | @ 1 |
| 82 | CH | C | 0 | H | 4-CONHPh | | 0.02 | | 41% | @ 1 |
| 83 | CH | C | 0 | H | 4-NHCONHPH | | 0.17 | | 25% | @ 1 |
| 84 | CH | C | 0 | H | 4-NHCO(4-Ph)Ph | | 35% | @ 1 | 2% | @ 1 |
| 85 | CH | C | 0 | H | 4-NHCO(3-CH$_3$)Ph | | 0.05 | | 0.38 | |
| 86 | CH | C | 0 | H | 4-OCH$_2$CH(CH$_3$)$_2$ | | 0.065 | | 10% | @ 1 |
| 87 | CH | C | 0 | H | 4-NHCO(4-CH$_3$)Ph | | 0.074 | | 47% | @ 1 |
| 88 | CH | C | 0 | 5-Cl | 4-NHCO(2-CH$_3$)Ph | | 0.043 | | 0.9 | |
| 89 | CH | C | 0 | 4,5-di-Cl | 4-NHCO(2-CH$_3$)Ph | | 35% | @ 1 | 2% | @ 1 |
| 90 | CH | C | 0 | 5-Cl | 3,4-di-(OCH$_3$) | | 0.1 | | 4% | @ 1 |
| 91 | CH | C | 0 | 4,5-di-Cl | 3,4-di-(OCH$_3$) | | 0.028 | | 0% | @ 1 |
| 92 | CH | C | 0 | H | 4-SCH$_3$ | | 0.066 | | 0% | @ 1 |
| 93 | CH | C | 0 | H | 4-NHCO(4-SCH$_3$)Ph | | 0.015 | | 26% | @ 1 |
| 94 | CH | C | 0 | H | 4-SOCH$_3$ | | 0.02 | | 10% | @ 1 |
| 95 | CH | C | 0 | H | 4-NHCO(4-SOCH$_3$)Ph | | 27% | @ 1 | 0% | @ 1 |
| 96 | CH | C | 0 | H | 4-NHCO(2-Cl)Ph | | 0.012 | | 0.180 | |
| 97 | CH | C | 0 | H | 4-NHCO(3,4-di-OCH$_3$)Ph | | 35% | @ 1 | 2% | @ 1 |

TABLE III-continued

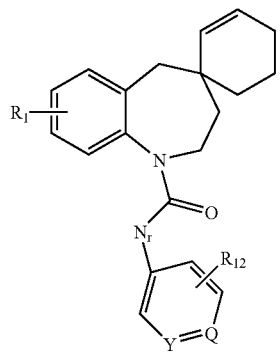

| Compound No. | Y | Q | r | $R_1$ | $R_{12}$ | V1a Functional Activity ($IC_{50}$ in µM) | Receptor Binding ($IC_{50}$ in µM or % Inh. @ concentration in µM) V1a | V2 |
|---|---|---|---|---|---|---|---|---|
| 98 | CH | C | 0 | H | 4-CCNH(2-$CH_3$)Ph | | 0.027 | 0.20 |
| 99 | CH | C | 0 | H | 4-NHCO(2,6-di-$OCH_3$)Ph | 0.08 | 0.041 | 35% @ 1 |
| 100 | CH | C | 0 | H | 4-NHCO(2-$CH_3$-4-F)Ph | 0.05 | 0.008 | 0.067 |
| 101 | CH | C | 0 | H | 4-NHCO(2-F)Ph | 0.06 | 0.010 | 0.550 |
| 102 | CH | C | 0 | H | 4-NHCO(2,6-di-Cl)Ph | | 0.046 | 0.159 |
| 103 | CH | C | 0 | H | 4-NHCO(2,4-di-Cl)Ph | | 0.016 | 0.274 |
| 104 | CH | C | 0 | H | 4-NHCO(4-pyridine) | | 0.051 | 36% @ 1 |
| 105 | CH | C | 0 | H | 4-NHCO(2-$CH_3$)$_3$-(pyridine) | | 0.035 | 1 |
| 106 | N | C | 1 | H | 2-$CH_3$-4-F | | 0.023 | 0.050 |
| 107 | CH | CH | 0 | H | 2-F | | 0.06 | 21% @ 1 |
| 108[1] | CH | C | 0 | H | 4-NHCO(2-F)Ph | | 0.024 | 0.57 |
| 109[1] | CH | C | 0 | H | 4-NHCO(2-F)Ph | | 0.014 | 0.30 |
| 110 | CH | C | 0 | H | 2-Cl-4-NHCO(2-F)Ph | 2.57 | 0.90 | 1 |
| 111 | CH | C | 0 | H | 2-Cl-4-NHCO(2-$CH_3$-5-F)Ph | | 0.80 | 0.045 |
| 112 | CH | C | 0 | H | 2-Cl-4-NHCO(2-$CH_3$)Ph | | 0.062 | 0.08 |
| 113 | CH | C | 0 | H | 2-Cl-4-NHCO(2-$CH_3$)-3-furane | | 0.041 | 28% @0.1 |
| 114 | CH | C | 0 | H | 4-NHCO(4-$CH_3$-Ph)Ph | | 0.090 | 0.095 |
| 115 | CH | C | 0 | H | 2-$OCH_3$-4-NHCO(2-F)Ph | | 0.019 | 37% @0.1 |
| 116 | CH | C | 0 | H | 2-$OCH_3$-4-NHCO(2-$CH_3$-5-F)Ph | | 0.019 | 0.091 |
| 117 | CH | C | 0 | H | 2-Cl-4-NHCO(4-$CH_3$Ph)Ph | | 30% @0.1 | 0.100 |
| 118 | CH | C | 0 | H | 2-Cl-4-NHCO(2-Ph)Ph | | 40% @ 0 | 0.085 |
| 119 | CH | C | 0 | 5-F | 2-Cl-4-NHCO(2-Ph)Ph | | 0.10 | 0.074 |
| 120 | CH | C | 0 | 5-F | 2-Cl-4-NHCO(2-$CH_3$-5-F)Ph | | 0.021 | 46% @0.1 |
| 121 | CH | C | 0 | 5-$OCH_3$ | 4-NHCO(2-Ph)Ph | | 26% @0.1 | 16% @0.1 |
| 122 | CH | C | 0 | 5-Cl | 4-NHCO(2-Ph)Ph | | 17% @0.1 | 26% @0.1 |
| 123 | CH | C | 0 | 4,5-di-Cl | 4-NHCO(2-Ph)Ph | | 18% @0.1 | 23% @0.1 |
| 124 | CH | C | 0 | 4-Cl | 2-Cl-4-NHCO(2-$CH_3$-5-F)Ph | | 26% @0.1 | 29% @0.1 |
| 125 | CH | C | 0 | 4-Cl | 4-NHCO(2-$CH_3$-5-F)Ph | | 0.032 | 46% @ 0 |
| 126 | CH | C | 0 | 4-Cl | 4-NHCO(2-$CH_3$)Ph | | 0.062 | 20% @ 0 |
| 127 | CH | C | 0 | H | 2-Cl-4-N$CH_3$CO(2-$CH_3$-5-F)Ph | | 0.065 | 0.1 |

[1]Enantiomer (determination of absolute stereochemistry pending)

TABLE IV

| Compound No. | $R_1$ | $R_{12}$ | Receptor Binding (IC$_{50}$ in μM or % Inh. @concentration in μM) V1a | V2 |
|---|---|---|---|---|
| 128 | H | 4-NHCO(2-F)Ph | 0.042 | 33% @ 0.1 |
| 129 | H | 4-NHCO(2-Ph)Ph | 30% @ 0.1 | 9% @ 0.1 |
| 130 | H | 4-NHCO(2-CH$_3$)Ph | 0.047 | 15% @ 0.1 |
| 131 | H | 4-NHCO(2-CH$_3$-5-F)Ph | 0.10 | 3% @ 0.1 |
| 132 | 5-OCH$_3$ | 4-NHCO(2-F)Ph | 0.10 | 1% @ 0.1 |

TABLE V

| Compound No. | Structure | MH$^+$ | Receptor Binding (IC$_{50}$ in μM or % Inh. @concentration in μM) V1a | V2 |
|---|---|---|---|---|
| 133 | 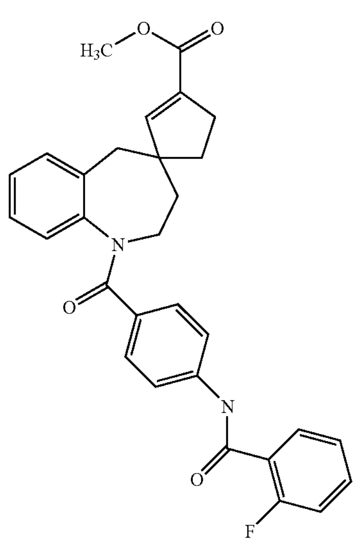 | 499 | 0.015 | 23% @ 0.1 |

TABLE V-continued

| Compound No. | Structure | MH+ | Receptor Binding (IC$_{50}$ in μM or % Inh. @concentration in μM) V1a | V2 |
|---|---|---|---|---|
| 134 | 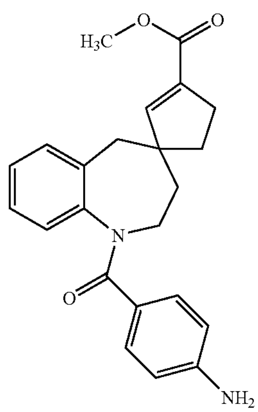 | 377 | 21% @ 0.1 | 16% @ 0.1 |
| 135 | 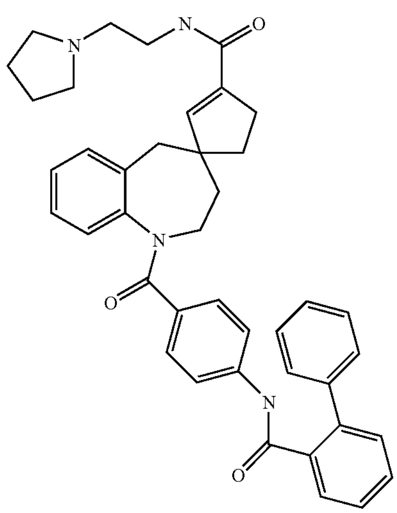 | 639 | 0.013 | 0.024 |
| 136 | 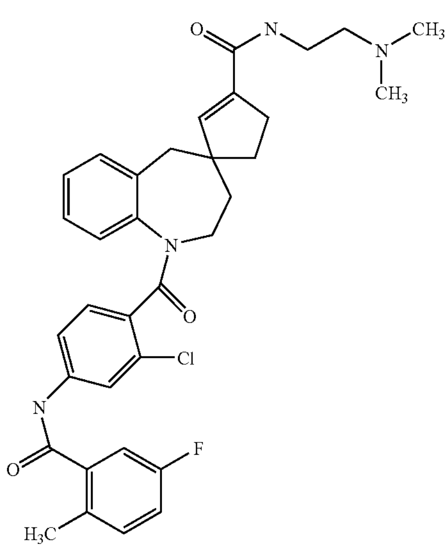 | 603 | 60% @ 0.1 | 0.052 |

TABLE V-continued
| Compound No. | Structure | MH+ | Receptor Binding (IC$_{50}$ in μM or % Inh. @concentration in μM) | |
|---|---|---|---|---|
| | | | V1a | V2 |
| 137 | 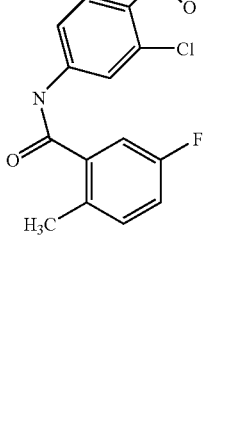 | 519 | 53% @ 0.1 | 66% @ 0.1 |
| 138 | 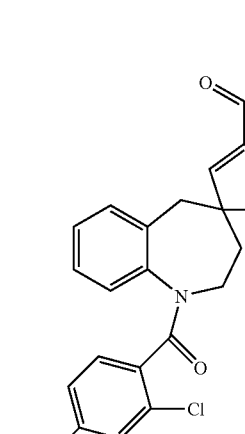 | 517 | 35% @ 0.1 | 57% @ 0.1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 139 | 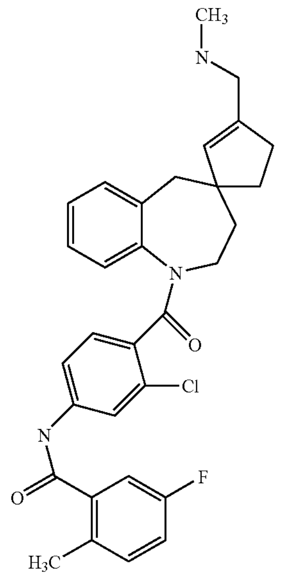 | 532 | 0% @ 0.1 | 17% @ 0.1 |
| 140 | 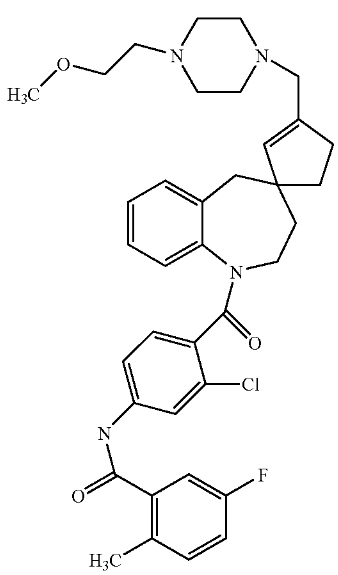 | 645 | 41% @ 0.1 | 65% @ 0.1 |

TABLE V-continued
| Compound No. | Structure | MH+ | Receptor Binding (IC$_{50}$ in μM or % Inh. @concentration in μM) | |
| --- | --- | --- | --- | --- |
| | | | V1a | V2 |
| 141 | 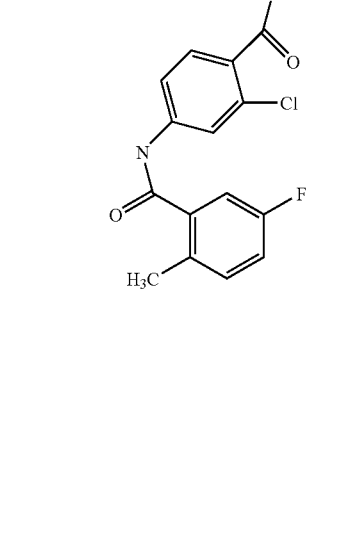 | 700 | 44% @ 0.1 | 0.056 |
| 142 | 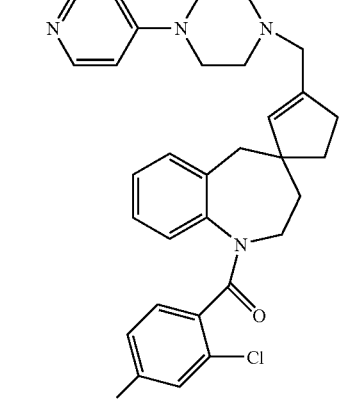 | 664 | 25% @ 0.1 | 69% @ 0.1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 143 | 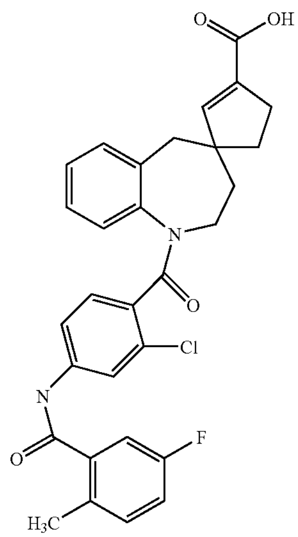 | 533 | 10% @ 0.1 | 67% @ 0.1 |
| 144 | 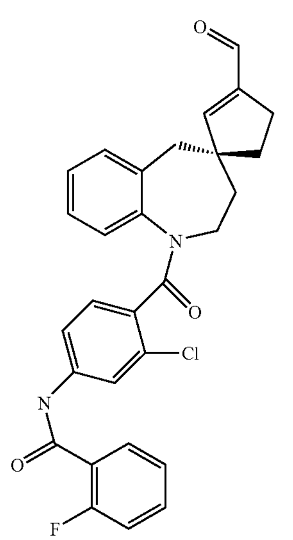 | 503 | 0.008 | 9% @ 0.1 |

TABLE V-continued
| Compound No. | Structure | MH+ | V1a | V2 |
|---|---|---|---|---|
| | | | Receptor Binding (IC$_{50}$ in μM or % Inh. @concentration in μM) | |
| 145 | 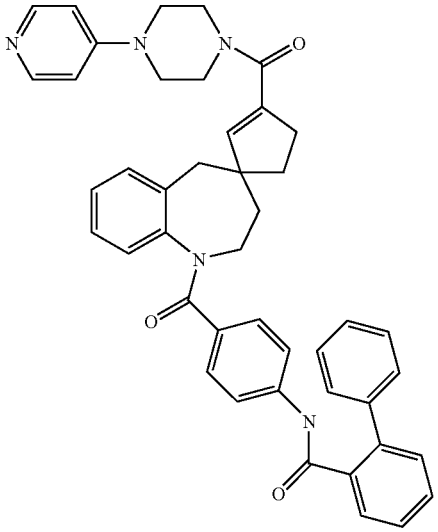 | 688 | 66% @ 0.1 | 0.066 |
| 146 | 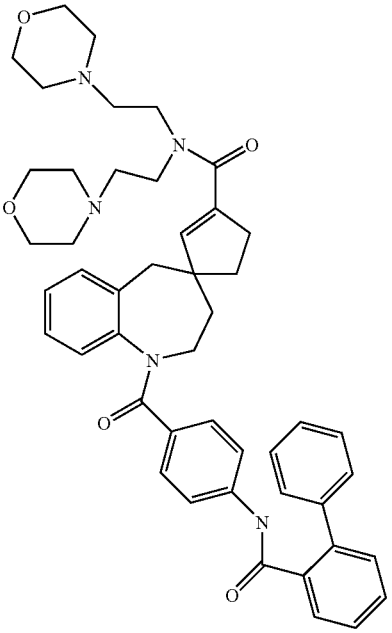 | 768 | 48% @ 0.1 | 39% @ 0.1 |

TABLE V-continued
| Compound No. | Structure | MH+ | V1a | V2 |
|---|---|---|---|---|
| 147 | 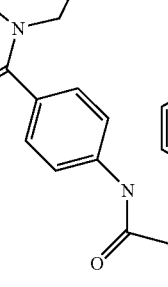 | 543 | | |
| 148 | 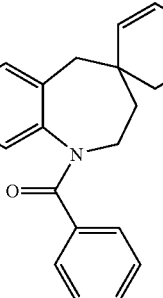 | 365 | | |
| 149 | 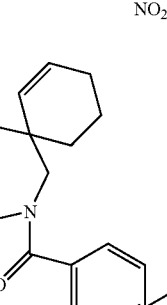 | 376 | 0.56 | 54% @ 1 |
| 150 | 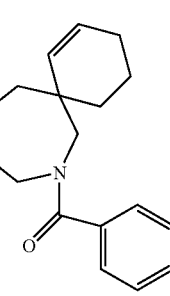 | 348 | | |
Receptor Binding (IC$_{50}$ in μM or % Inh. @concentration in μM)

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 151 | 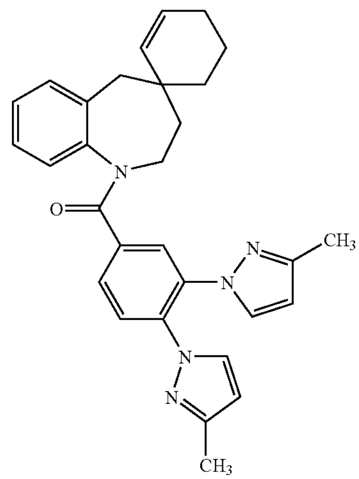 | 478 | 0.042 | 20% @ 1 |
| 152 | 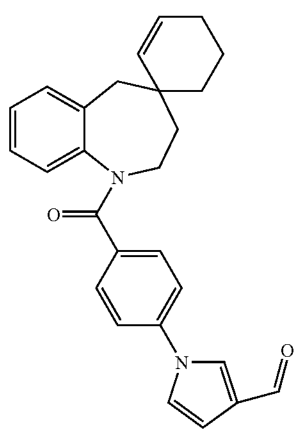 | 411 | 0.084 | 13% @ 1 |
| 153 | 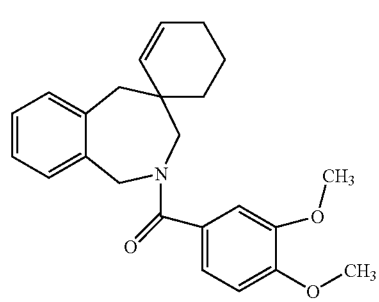 | 378 | 0.55 | 0% @ 1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 154 | 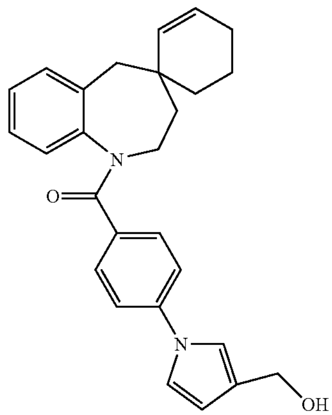 | 413 | 0.025 | 36% @ 1 |
| 155 | 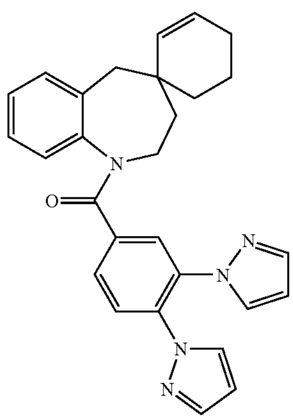 | 450 | 0.13 | 2% @ 1 |
| 156 | 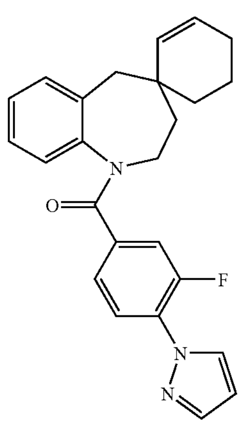 | 402 | 0.11 | 13% @ 1 |

TABLE V-continued
| Compound No. | Structure | MH+ | Receptor Binding (IC$_{50}$ in μM or % Inh. @concentration in μM) | |
|---|---|---|---|---|
| | | | V1a | V2 |
| 157 | 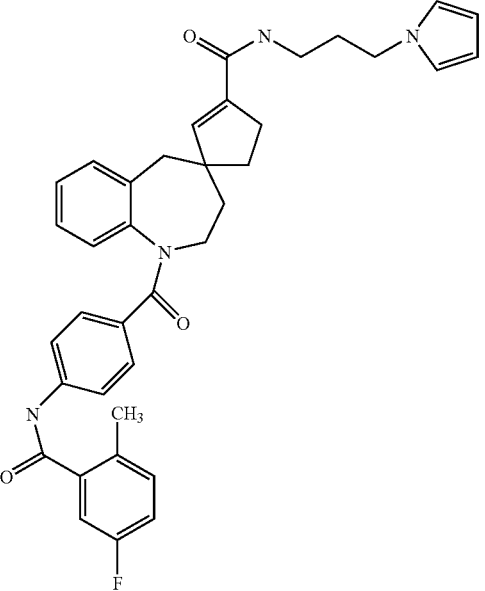 | 609 | 0.016 | 0.038 |
| 158 | 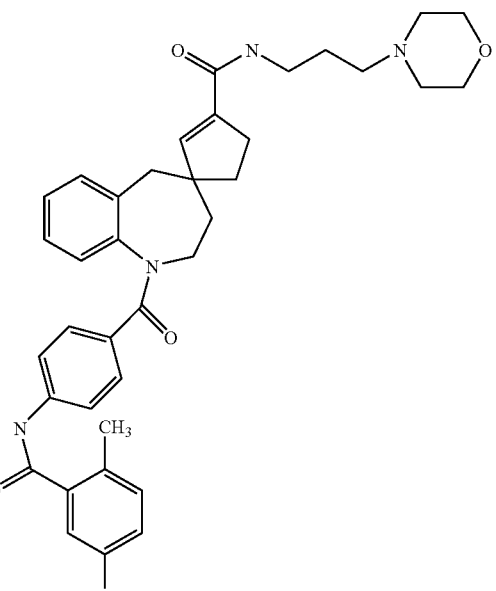 | 625 | 0.016 | 0.039 |

TABLE V-continued
| Compound No. | Structure | MH+ | Receptor Binding (IC₅₀ in μM or % Inh. @concentration in μM) | |
|---|---|---|---|---|
| | | | V1a | V2 |
| 159 | 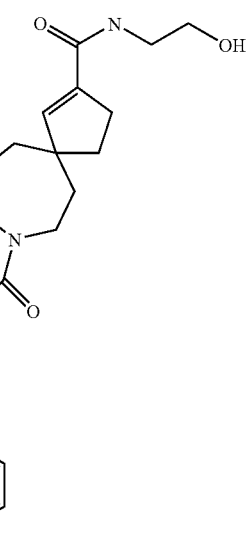 | 542 | 0.011 | 0.047 |
| 160 | 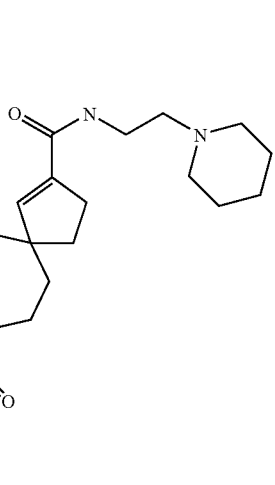 | 609 | 0.011 | 0.082 |

TABLE V-continued
| Compound No. | Structure | MH+ | Receptor Binding (IC$_{50}$ in μM or % Inh. @concentration in μM) | |
| --- | --- | --- | --- | --- |
| | | | V1a | V2 |
| 161 | 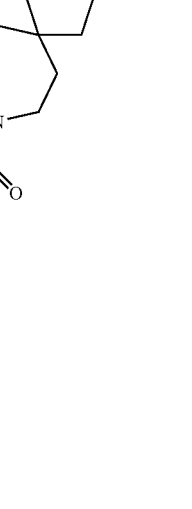 | 595 | 0.01 | 0.072 |
| 162 | 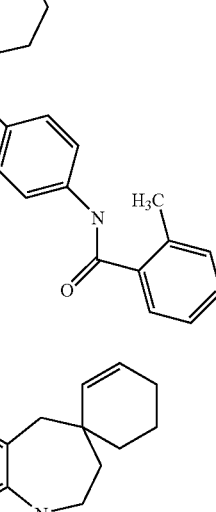 | 509 | 0.069 | 42% @ 0.25 |
| 163 | 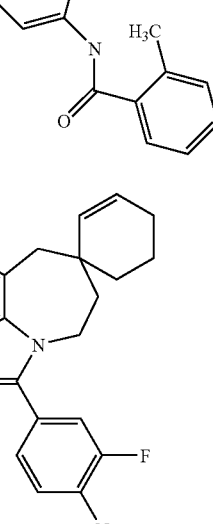 | 402 | | |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 164 | 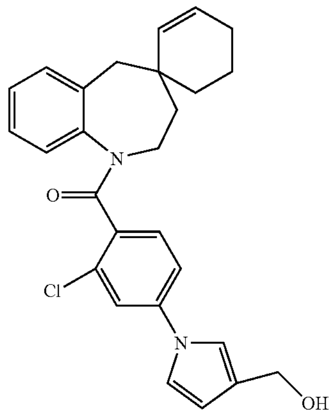 | 447 | 0.114 | 20% @ 0.25 |
| 165 | 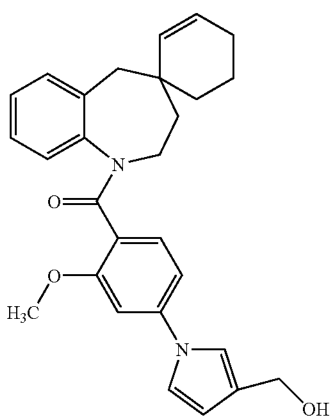 | 443 | 0.042 | 25% @ 0.25 |
| 166 | 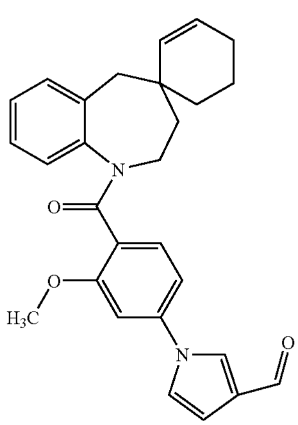 | 441 | 0.114 | 5% @ 0.25 |

TABLE V-continued
| Compound No. | Structure | MH+ | Receptor Binding (IC$_{50}$ in μM or % Inh. @concentration in μM) | |
|---|---|---|---|---|
| | | | V1a | V2 |
| 167 | 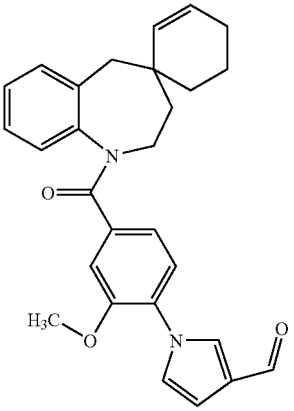 | 441 | 0.06 | 19% @ 0.25 |
| 168 | 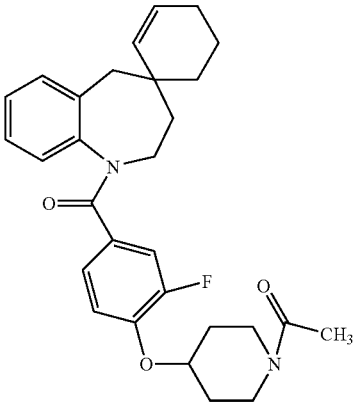 | 477 | 50% @ 0.1 | 0% @ 1 |
| 169 | 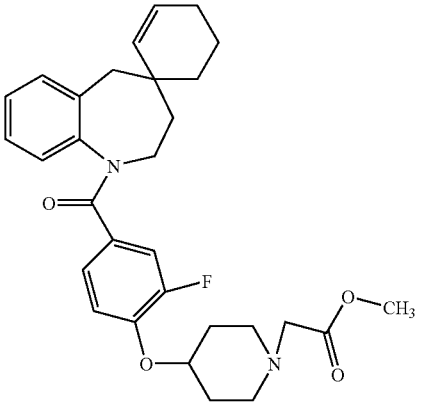 | 507 | 4% @ 0.1 | 0% @ 1 |

TABLE V-continued

| Compound No. | Structure | MH+ | Receptor Binding (IC$_{50}$ in μM or % Inh. @concentration in μM) V1a | V2 |
|---|---|---|---|---|
| 170 | 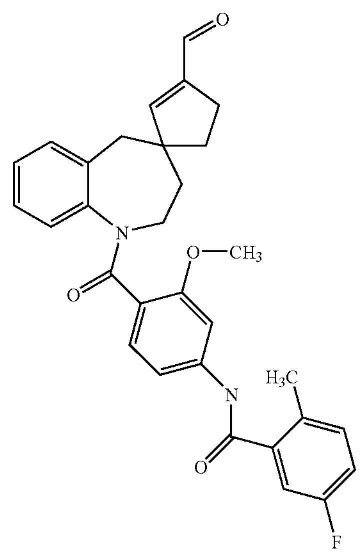 | 513 | 0.055 | 0.21 |
| 171 | 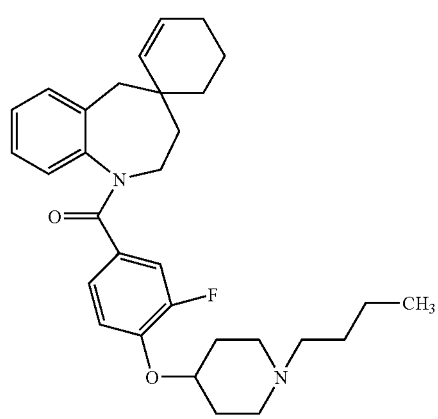 | 491 | 24% @ 0.1 | 65% @ 1 |
| 172 | 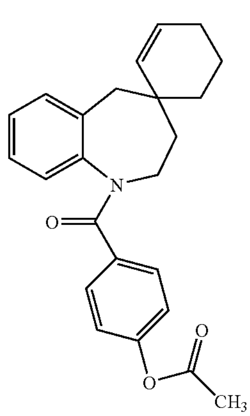 | 376 | 15% @ 0.1 | 0% @ 1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 173 | 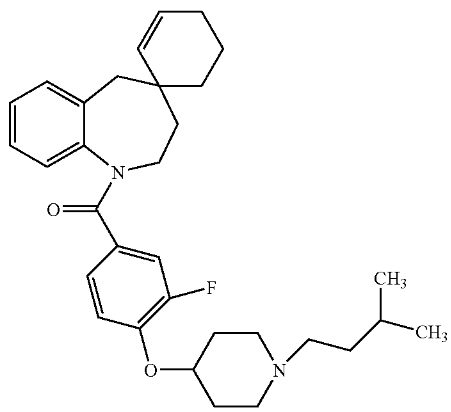 | 505 | 0% @ 0.1 | 0% @ 1 |
| 174 | 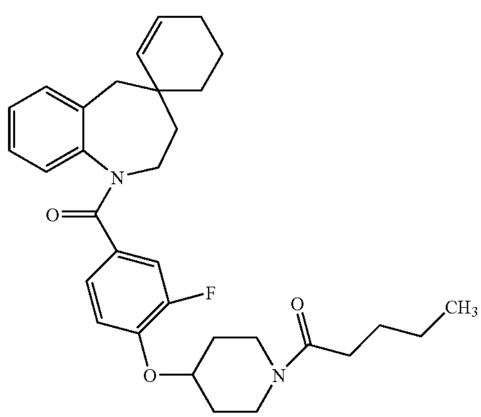 | 519 | 0% @ 0.1 | 8% @ 1 |
| 175 | 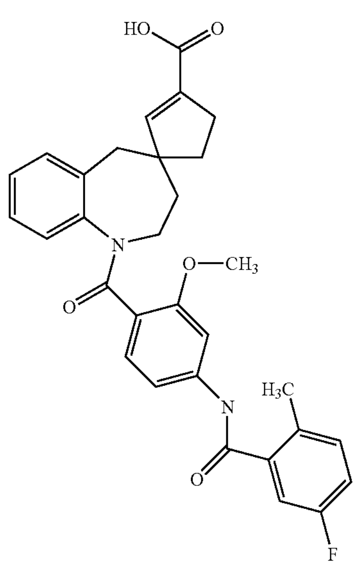 | 529 | 15% @ 0.1 | 0.11 |

TABLE V-continued

| Compound No. | Structure | MH+ | Receptor Binding (IC50 in μM or % Inh. @concentration in μM) | |
|---|---|---|---|---|
| | | | V1a | V2 |
| 176 | 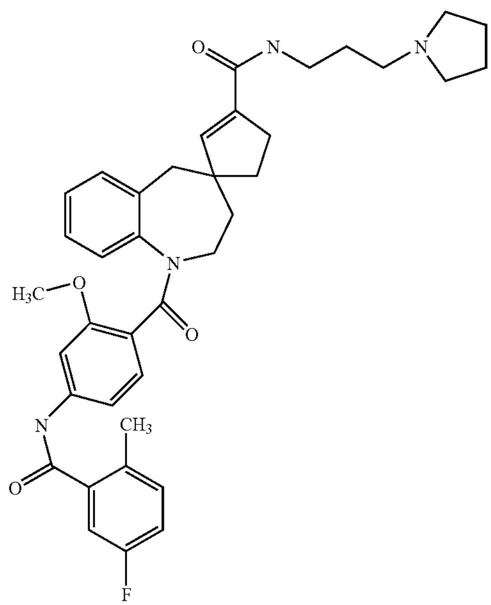 | 639 | 0.011 | 0.062 |
| 177 | 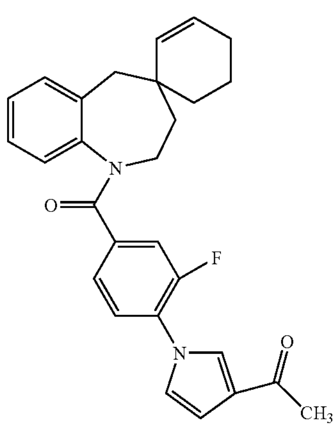 | 443 | 0.044 | 30% @ 1 |
| 178 | 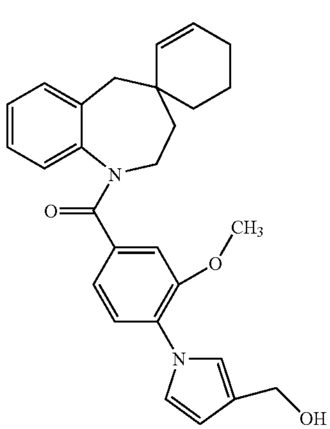 | 443 | 0.013 | 53% @ 1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 179 | 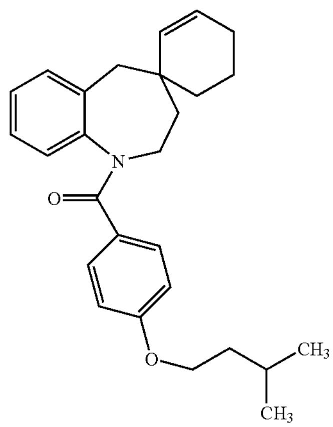 | 404 | 0.096 | 15% @ 1 |
| 180 | 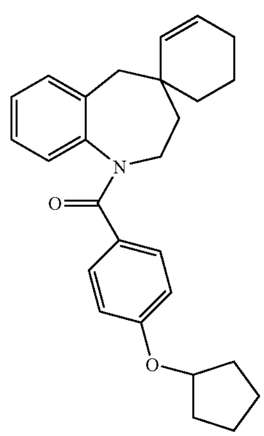 | 402 | 0.088 | 20% @ 1 |
| 181 | 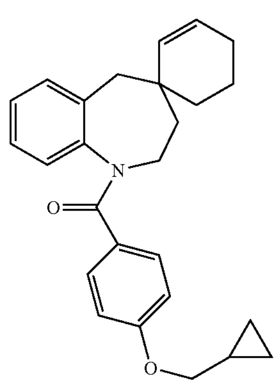 | 388 | 0.066 | 31% @ 1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 182 | 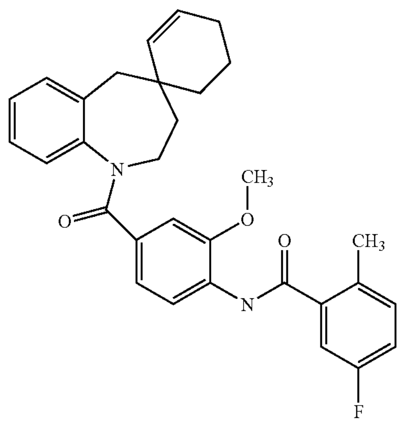 | 499 | 0.062 | 0.228 |
| 183 | 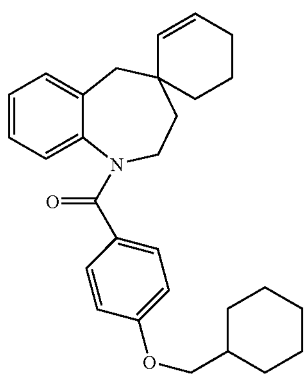 | 430 | 0.25 | 18% @ 1 |
| 184 | 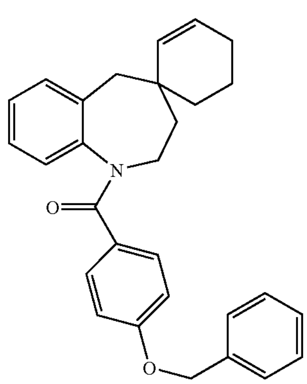 | 424 | 0.086 | 34% @ 1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 185 | 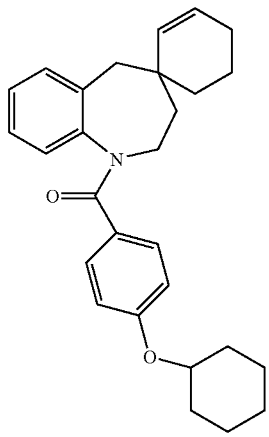 | 416 | 0.23 | 42% @ 1 |
| 186 | 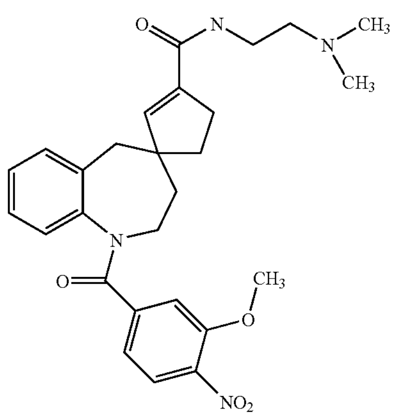 | 493 | 48% @ 1 | 11% @ 1 |
| 187 | 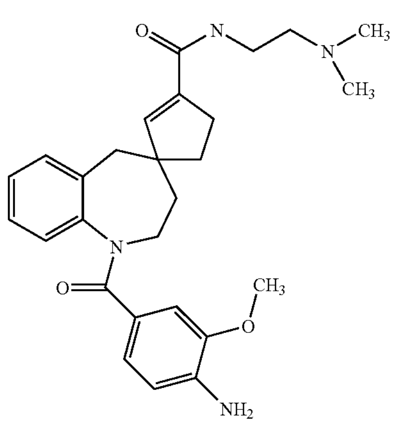 | 463 | 54% @ 1 | 7% @ 1 |

TABLE V-continued

| Compound No. | Structure | MH+ | Receptor Binding (IC$_{50}$ in μM or % Inh. @concentration in μM) | |
| --- | --- | --- | --- | --- |
| | | | V1a | V2 |
| 188 | 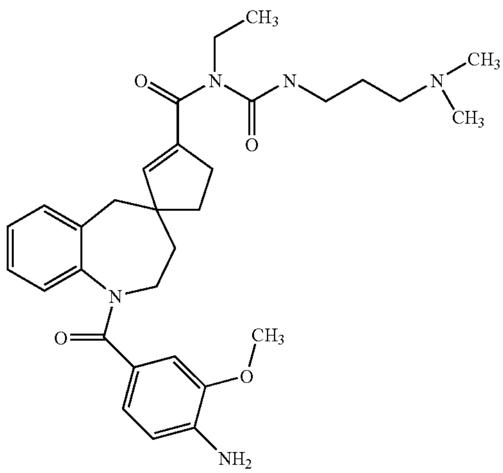 | 548 | 27% @ 1 | 3% @ 1 |
| 189 | 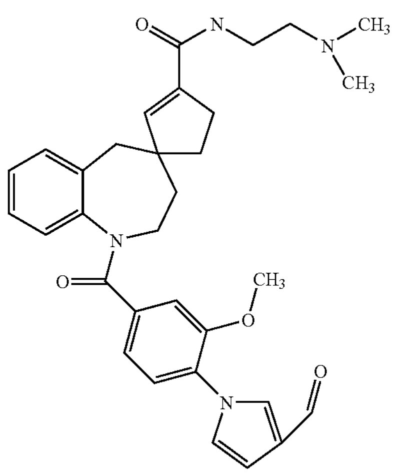 | 541 | 0.045 | 13% @ 1 |
| 190 | 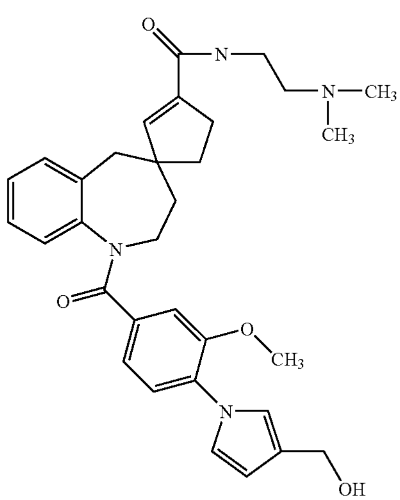 | 543 | 0.008 | 28% @ 1 |

TABLE V-continued

| Compound No. | Structure | MH+ | Receptor Binding (IC$_{50}$ in μM or % Inh. @concentration in μM) | |
| --- | --- | --- | --- | --- |
| | | | V1a | V2 |
| 191 | 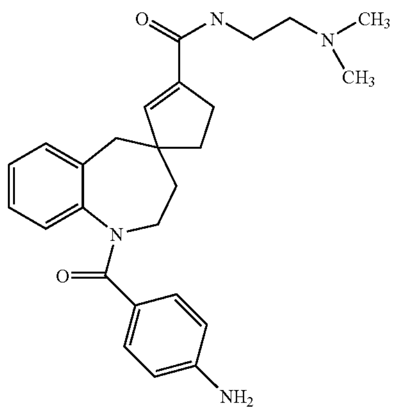 | 433 | 1.2 | 15% @ 1 |
| 192 | 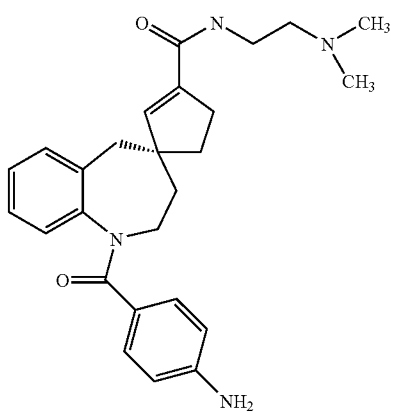 | 433 | 5.4 | 0% @ 1 |
| 193 | 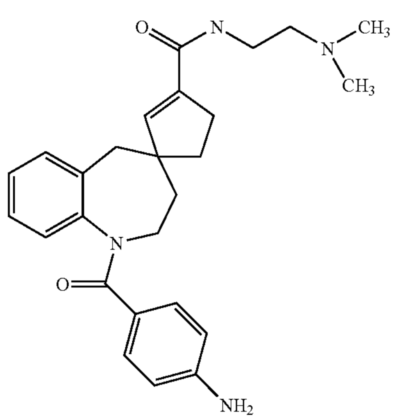 | 433 | 1.1 | 0% @ 1 |

TABLE V-continued

| Compound No. | Structure | MH+ | Receptor Binding (IC₅₀ in μM or % Inh. @concentration in μM) | |
| --- | --- | --- | --- | --- |
| | | | V1a | V2 |
| 194 | 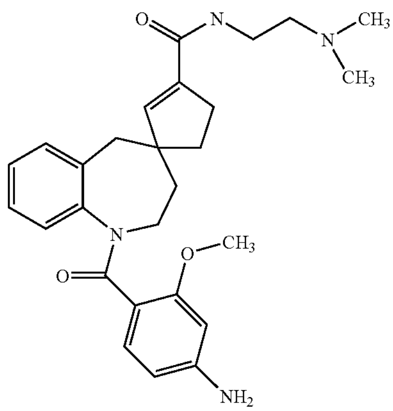 | 463 | 7% @ 1 | 6% @ 1 |
| 195 | 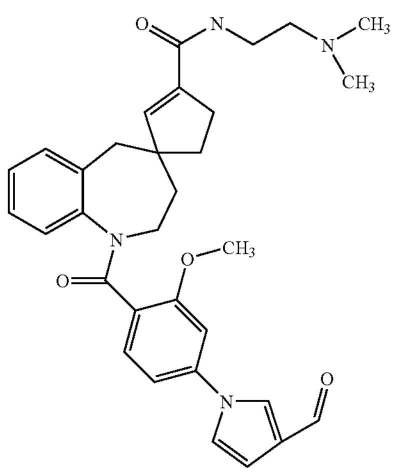 | 541 | 0.3 | 18% @ 1 |
| 196 | 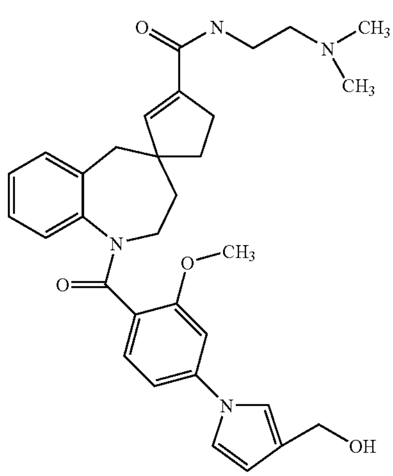 | 543 | 0.034 | 34% @ 1 |

TABLE V-continued
| Compound No. | Structure | MH+ | Receptor Binding (IC$_{50}$ in μM or % Inh. @concentration in μM) | |
| --- | --- | --- | --- | --- |
| | | | V1a | V2 |
| 197 | 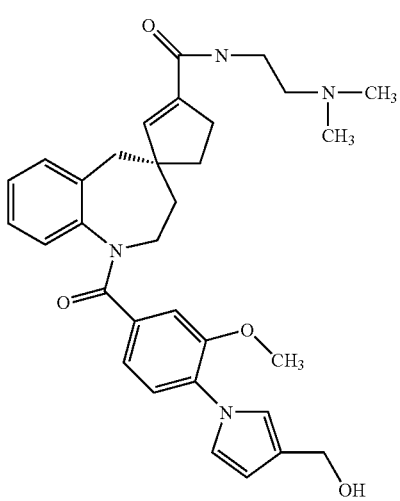 | 543 | 0.006 | 0% @ 0.1 |
| 198 | Chiral<br>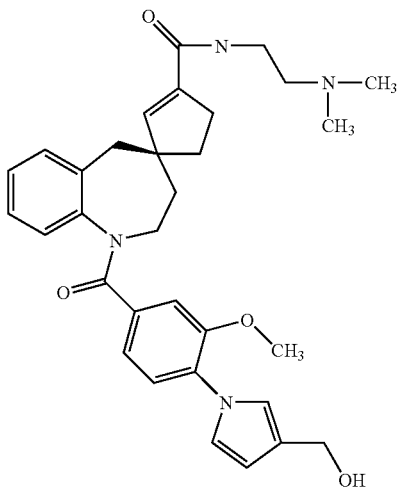 | 543 | 0.016 | 0% @ 0.1 |
| 199 | 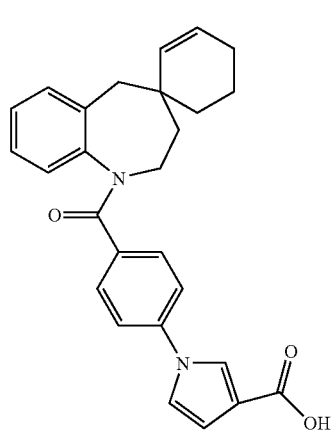 | 427 | 0% @ 0.1 | 2% @ 0.1 |

TABLE V-continued

| Compound No. | Structure | MH+ | Receptor Binding (IC₅₀ in μM or % Inh. @concentration in μM) | |
| --- | --- | --- | --- | --- |
| | | | V1a | V2 |
| 200 | 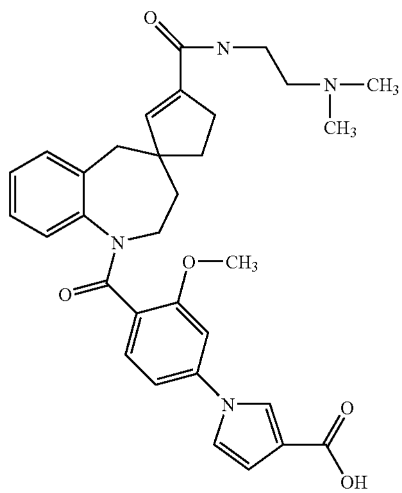 | 557 | 0% @ 0.1 | |
| 201 | 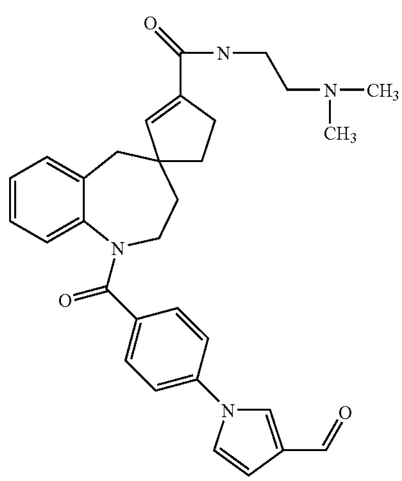 | 511 | 44% @ 0.1 | 0% @ 0.1 |
| 202 | 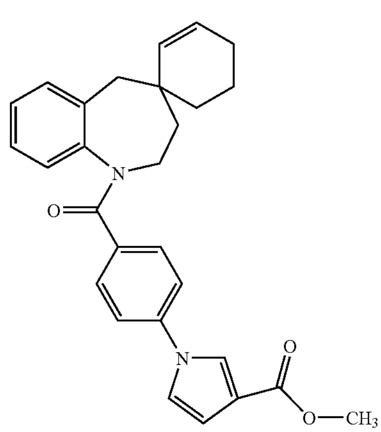 | 441 | 22% @ 0.1 | |

TABLE V-continued

| Compound No. | Structure | MH+ | Receptor Binding (IC$_{50}$ in μM or % Inh. @concentration in μM) V1a | V2 |
|---|---|---|---|---|
| 203 | 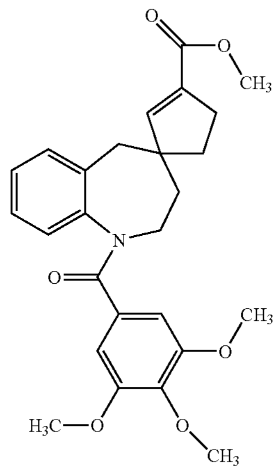 | 452 | 3% @ 0.1 | |
| 204 | 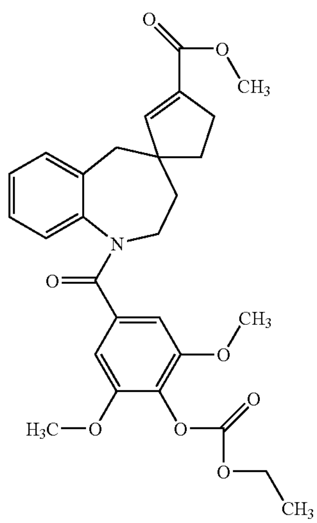 | 510 | 0% @ 0.1 | |
| 205 | 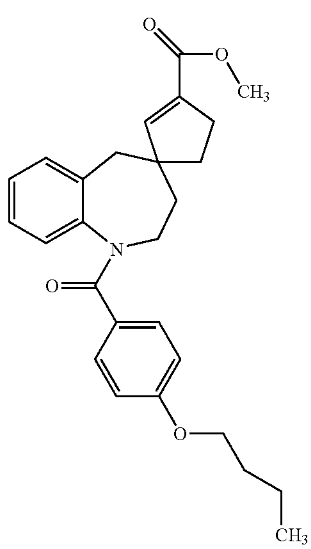 | 434 | 0.14 | |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 206 | 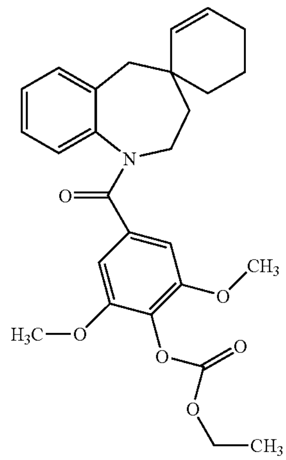 | 466 | 9% @ 0.1 | |
| 207 | 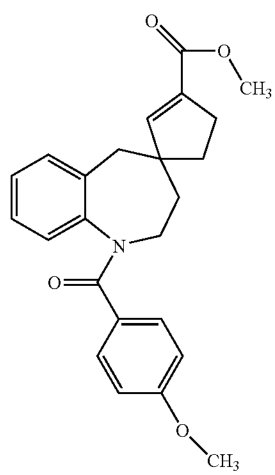 | 392 | | |
| 208 | 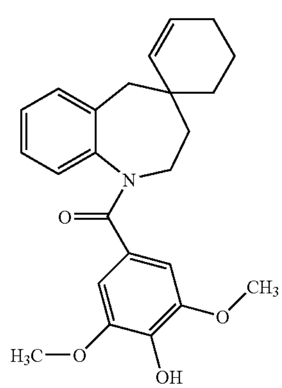 | 394 | | |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 209 | 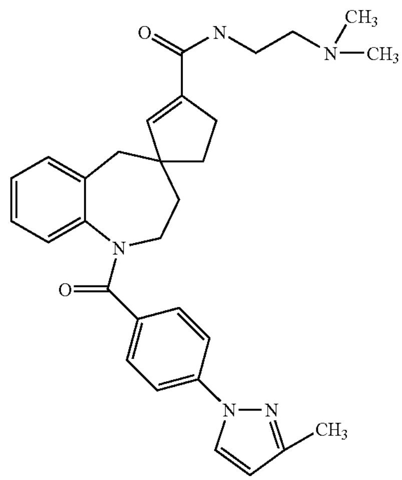 | 498 | 0.055 | 43% @ 1 |
| 210 | 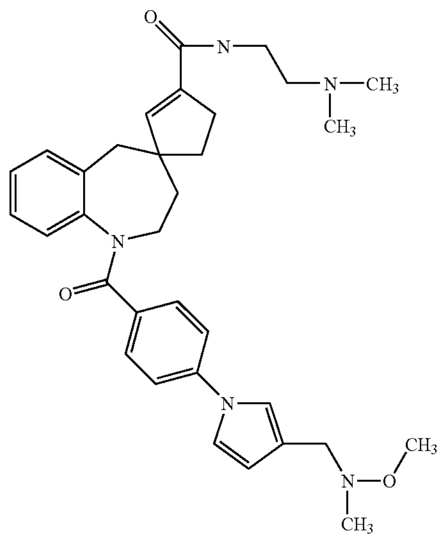 | 556 | 6% @ 0.125 | 22% @ 1 |
| 211 | 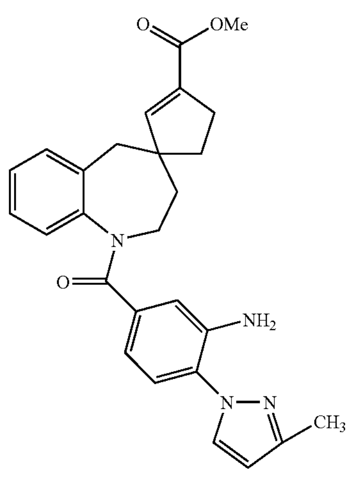 | 457 | 55% @ 0.125 | 45% @ 1 |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 212 | 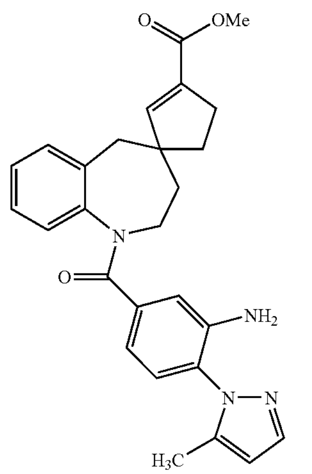 | 457 | 29% @ 0.125 | 16% @ 1 |
| 213 | 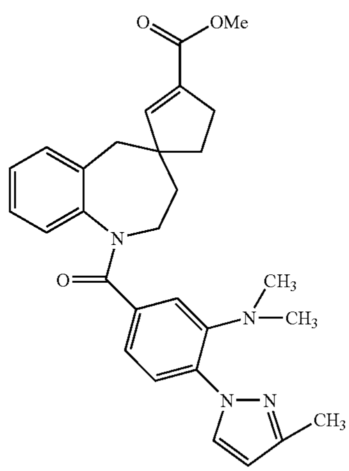 | 485 | 63% @ 0.125 | 55% @ 1 |
| 214 | 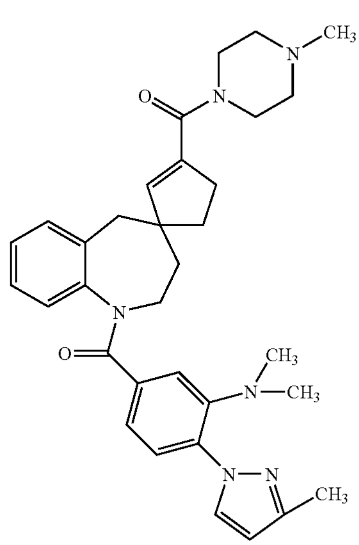 | 553 | 48% @ 0.1 | |

TABLE V-continued

| Compound No. | Structure | MH+ | Receptor Binding (IC$_{50}$ in μM or % Inh. @concentration in μM) | |
|---|---|---|---|---|
| | | | V1a | V2 |
| 215 | 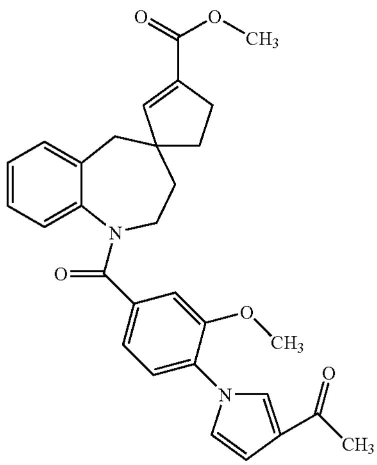 | 499 | 64% @ 0.1 | |
| 216 | 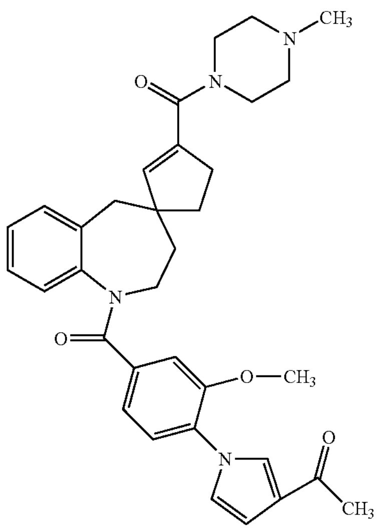 | 567 | 6% @ 0.1 | |
| 217 | 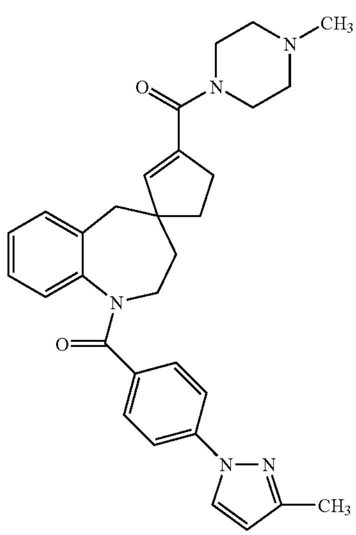 | 510 | 42% @ 0.1 | |

TABLE V-continued

| Compound No. | Structure | MH+ | Receptor Binding (IC$_{50}$ in μM or % Inh. @concentration in μM) ||
| | | | V1a | V2 |
| --- | --- | --- | --- | --- |
| 218 | | 517 | 0.046 | 23% @ 0.2 |
| 219 | | 503 | | 48% @ 0.2 |

TABLE V-continued
| Compound No. | Structure | MH+ | Receptor Binding (IC$_{50}$ in µM or % Inh. @concentration in µM) V1a | V2 |
|---|---|---|---|---|
| 220 | 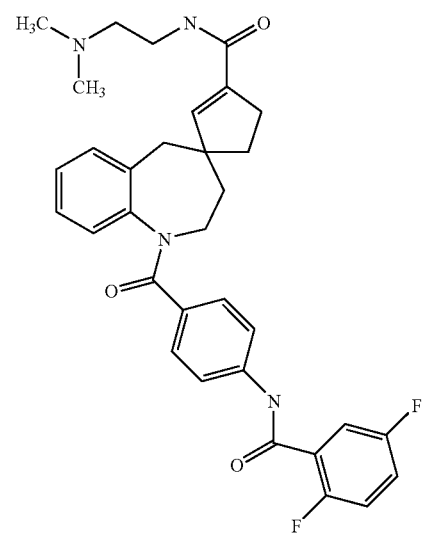 | 573 | 0.013 | |
| 221 | 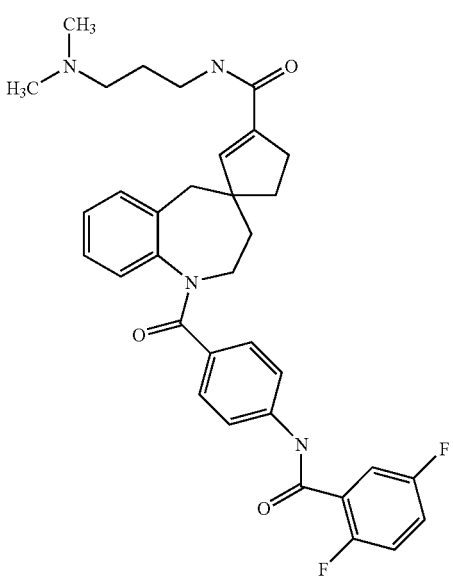 | 587 | 0.009 | |

TABLE V-continued
| Compound No. | Structure | MH+ | Receptor Binding (IC$_{50}$ in μM or % Inh. @concentration in μM) | |
|---|---|---|---|---|
| | | | V1a | V2 |
| 222 | 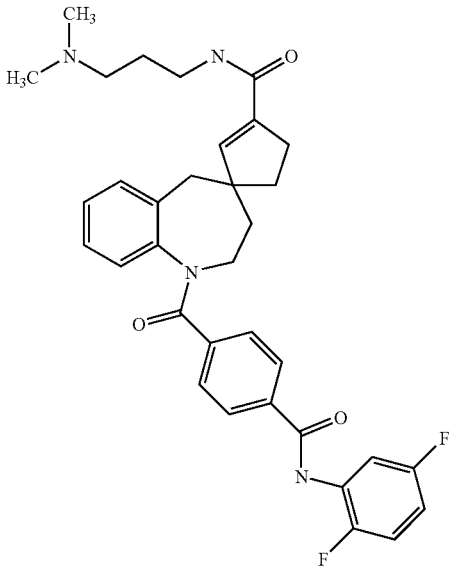 | 587 | | |
| 223 | 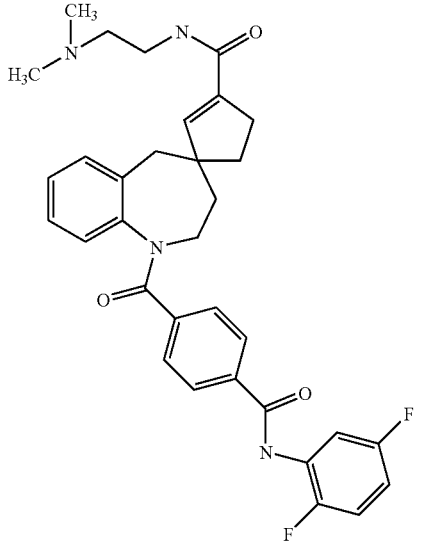 | 573 | | |

TABLE VI

| Compound No. | Structure | MH+ | Receptor Binding (IC$_{50}$ in μM or % Inh. @concentration in μM) | |
|---|---|---|---|---|
| | | | V1a | V2 |
| 224 | 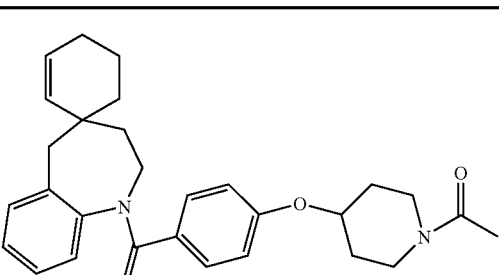 | 459 | 41% @ 0.1 | 0% |

EXAMPLE 50

V2 Vasopressin Receptor Functional Activity

The V2 receptor is also a G-protein coupled receptor which when activated induces an increase in cAMP turnover. Antagonism against the V2 receptor is determined by measuring cAMP accumulation in transfected HEK-293 cells expressing the human V2 receptor (V2-HEK cells). Compounds are tested for their ability to block the stimulatory effects of vasopressin on cAMP accumulation. The cell content of cAMP is measured by radioimmunoassay using NEN flashplates.

EXAMPLE 51

Reversal of Vasopressin-Induced Hypertension in Rats

The anti-hypertensive activity of a compound may be assessed using an anesthetized model of vasopressin-induced hypertension. Male Long Evans, normotensive rats of between 350 and 450 g in body weight may be anesthetized with pentobarbital (35 mg/kg, ip) and maintained throughout the procedure with an ip infusion of 10 mg/kg/hr. Arginine vasopressin (AVP) can be infused at 30 ng/kg/min, iv, to induce a stable hypertensive state (ca. 50 mmHg increase in mean arterial blood pressure). Compounds of interest can be administered in an ascending dose fashion and the maximum decrease in mean arterial blood pressure can be recorded. An ED$_{50}$ may be determined from the linear portion of the dose-response relationship for each animal.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I),

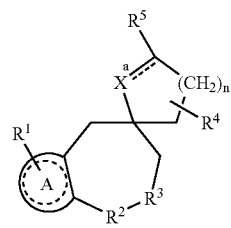

wherein
R$^1$ is one to three members independently selected from hydrogen, halogen, amino, substituted amino, hydroxy, alkyloxy, phenyl, substituted phenyl, alkylthio, arylthio, alkyl-sulfoxide, aryl-sulfoxide, alkyl-sulfone, and aryl-sulfone;

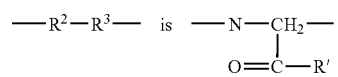

wherein
R' is -B$_p$-G-E$_q$-W wherein
(a) B is selected from (CH$_2$)$_m$, NH and O;
(b) G is selected from aryl, substituted aryl, heteroaryl, and substituted heteroaryl;
(c) E is O, S, NH, (CH$_2$)$_i$N(R")CO or (CH$_2$)$_i$CONR" wherein
R" is selected from hydrogen, alkyl, and substituted alkyl;
(d) W is one to three members independently selected from hydrogen, alkyl, substituted alkyl, amino, substituted amino, alkylthiophenyl, alkyl-sulfoxidephenyl, aryl, substituted aryl heteroaryl and substituted heteroaryl;

(e) p is independently 0 or 1;
(f) q is independently 0 or 1;
(g) m is independently 1, 2, or 3; and
(h) i is independently 0, 1, 2, or 3;
$R^4$ is one or two members independently selected from the group consisting of hydrogen, alkyl, substituted alkyl, phenyl, and substituted phenyl;
$R^5$ is selected from hydrogen, alkyl, substituted alkyl, aldehyde, carboxyl, alkoxycarbonyl, substituted alkoxycarbonyl, $-(CH_2)_k NZ^1 Z^2$ and $-CONZ^1 Z^2$ wherein k is an integer from 1-4, and $Z^1$ and $Z^2$ are independently selected from hydrogen, alkyl, substituted alkyl, heterocyclyl, substituted heterocyclyl, aminocarbonyl, and substituted aminocarbonyl, or N, $Z^1$ and $Z^2$ together form heterocyclyl, substituted heterocyclyl, heteroaryl, or substituted heteroaryl;
a represents a single or double bond provided that when $R^1$ is iodine, bromine, alkylthio, arylthio, alkyl-sulfone, or aryl-sulfone, a is a double bond;
A is selected from phenyl or substituted phenyl;
X is selected from CH, $CH_2$, CHOH, and C=O; and
n is 1, 2, or 3;
or an optical isomer, enantiomer, diastereomer, racemate thereof, or a pharmaceutically acceptable salt thereof.

2. The compound of claim 1 wherein a is a double bond.
3. The compound of claim 2 wherein
(a) p is 0 and q is 1;
(b) G is phenyl or substituted phenyl;
(c) E is NHCO; and
(d) W is phenyl or substituted phenyl.
4. The compound of claim 3 wherein $R^5$ is $-CONZ^1Z^2$ wherein $Z^1$ and $Z^2$ are as claimed in claim 1.
5. The compound of claim 1 wherein X is selected from $CH_2$, CHOH, and C=O.
6. The compound of claim 1 wherein
$R^1$ is H;
$R^4$ is H;
$R^5$ is H;
R' is $-B_p-G-E_q-W$ wherein
(a) W is phenyl or substituted phenyl;
(b) E is NHCO; and
(c) p is 0.
7. The compound of claim 1 wherein n is 1 or 2.
8. The compound of claim 7 wherein n is 1 and a is a double bond.

9. A pharmaceutical composition comprising a compound according to claim 1 and a pharmaceutically acceptable carrier.

10. A process for making a pharmaceutical composition comprising mixing any of the compounds according to claim 1 and a pharmaceutically acceptable carrier.

11. An intermediate of a formula selected from

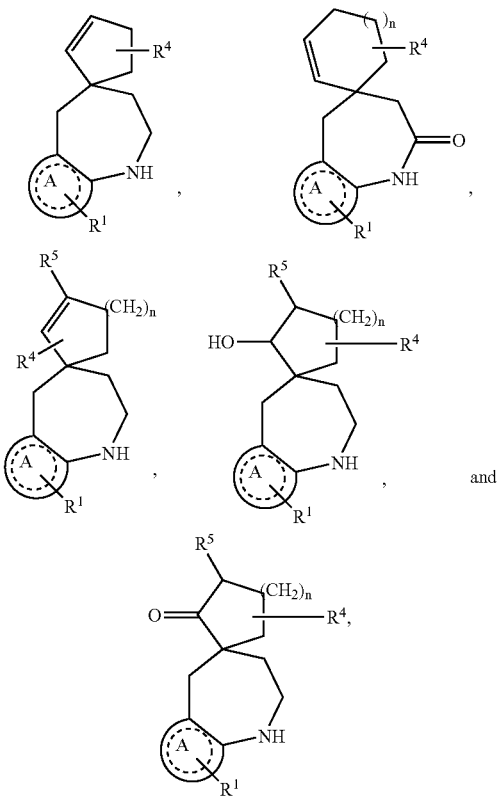

wherein, $R^1$, $R^4$, $R^5$, A, and n are claimed in claim 1.

* * * * *